US008102525B2

(12) United States Patent
Guo et al.

(10) Patent No.: US 8,102,525 B2
(45) Date of Patent: Jan. 24, 2012

(54) SYSTEMS AND METHODS FOR DETECTING CHEMICAL AND BIOLOGICAL SUBSTANCES

(75) Inventors: Xun Guo, Sacramento, CA (US); Hong Wang, Cupertino, CA (US); Chunwei Liu, Beijing (CN)

(73) Assignee: OptoTrace (SuZhou) Technologies, Inc., SuZhou (CN)

( * ) Notice: Subject to any disclaimer, the term of this patent is extended or adjusted under 35 U.S.C. 154(b) by 488 days.

(21) Appl. No.: 12/403,522

(22) Filed: Mar. 13, 2009

(65) Prior Publication Data

US 2010/0085564 A1    Apr. 8, 2010

(51) Int. Cl.
*G01J 3/44* (2006.01)
(52) U.S. Cl. ..................................... 356/301
(58) Field of Classification Search .................... 356/301
See application file for complete search history.

(56) References Cited

U.S. PATENT DOCUMENTS

| | | | |
|---|---|---|---|
| 4,933,274 A | 6/1990 | Sanford | |
| 5,017,007 A | 5/1991 | Milne | |
| 5,244,788 A | 9/1993 | Hubscher | |
| 5,527,712 A | 6/1996 | Sheehy | |
| 5,864,397 A | 1/1999 | Vo-Dinh | |
| 6,361,861 B2 | 3/2002 | Gao | |
| 6,406,777 B1 | 6/2002 | Boss | |
| 6,614,523 B1 | 9/2003 | Boss | |
| 2002/0123050 A1 | 9/2002 | Poponin | |
| 2003/0059820 A1 | 3/2003 | Vo-Dinh | |
| 2003/0175472 A1 | 9/2003 | Den | |
| 2004/0106203 A1 | 6/2004 | Stasiak | |
| 2004/0179195 A1* | 9/2004 | Su et al. | 356/301 |
| 2005/0136552 A1 | 6/2005 | Buechler | |
| 2006/0240572 A1* | 10/2006 | Carron et al. | 356/301 |
| 2007/0048746 A1* | 3/2007 | Su et al. | 435/6 |
| 2007/0247620 A1* | 10/2007 | Koo | 356/301 |
| 2008/0096005 A1* | 4/2008 | Premasiri | 356/301 |

* cited by examiner

*Primary Examiner* — Kara E Geisel
(74) *Attorney, Agent, or Firm* — SV Patent Service

(57) ABSTRACT

A method for detecting an ingredient in a food product or detecting a disease includes allowing a food sample solution obtained from a food product or a body fluid from an individual to come to contact with a nano-scale surface structure in a sensor, wherein the nano-scale surface structure comprises a plurality of columns over a substrate or a plurality of holes in a substrate. The method includes illuminating the food sample solution or the body fluid on the nano-scale surface structure on the sensor by a laser beam; obtaining a Raman spectrum from the scattered light using a spectral analyzer; and identifying the spectral signature in the Raman spectrum to determine the existence of the chemical substance in the food product or identifying a disease in the individual.

28 Claims, 31 Drawing Sheets

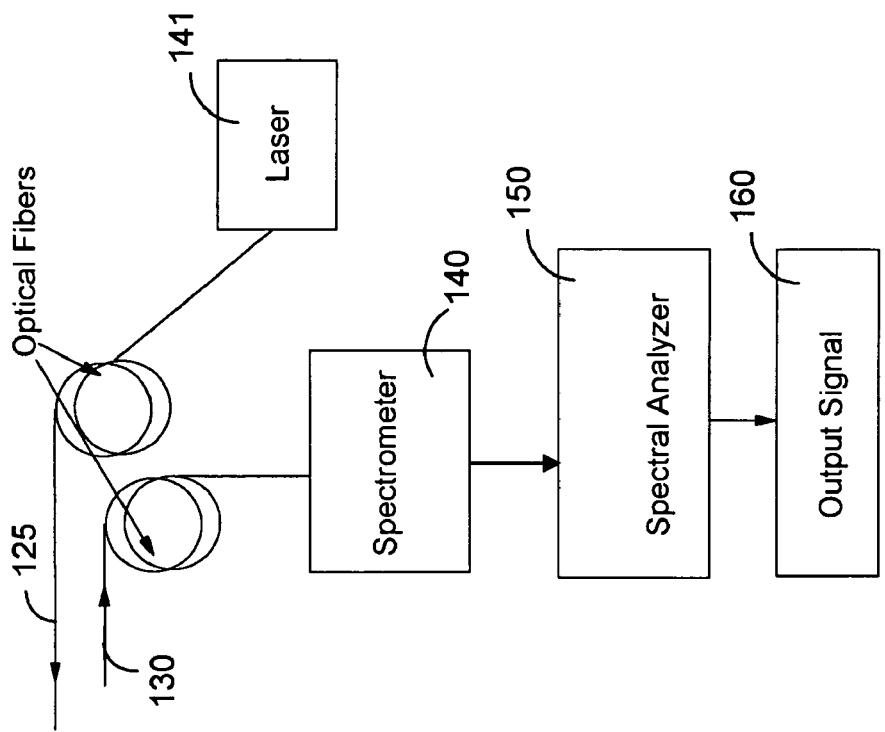
Fig. 1C
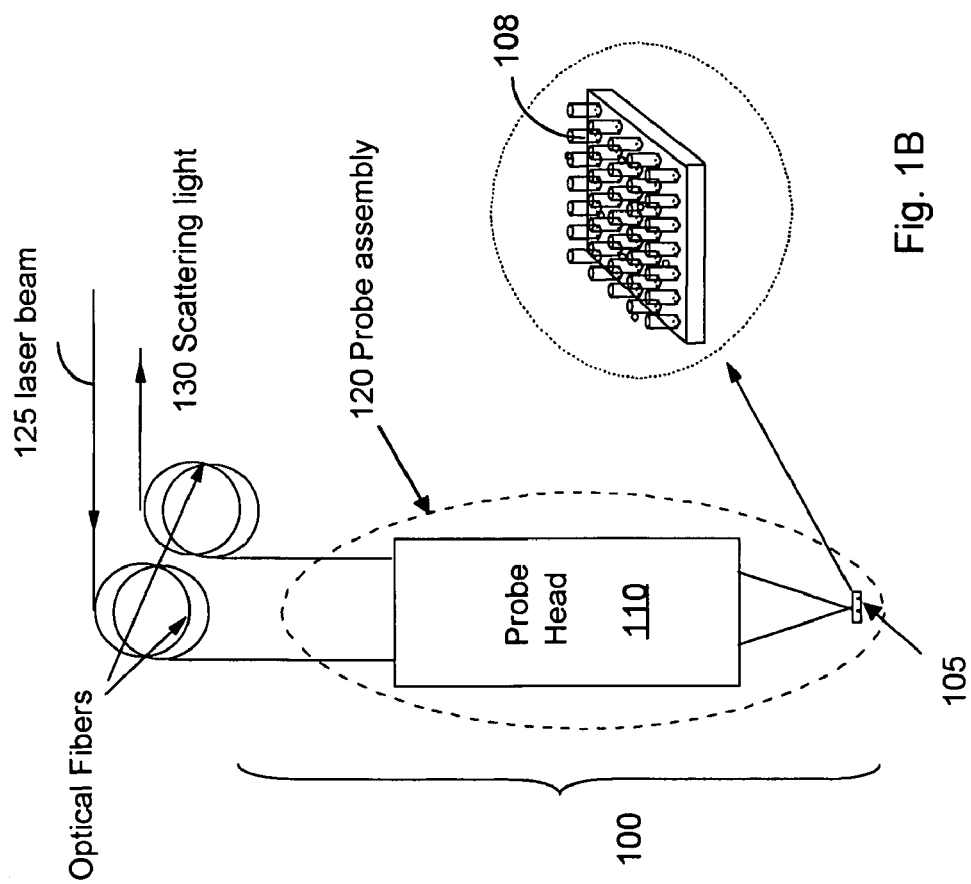
Fig. 1B
Fig. 1A

SECTION A-A

SYSTEMS AND METHODS FOR DETECTING CHEMICAL AND BIOLOGICAL SUBSTANCES

BACKGROUND

This invention relates generally to methods and systems for detecting chemical or biological substances by employing a light scattering probe and a chemical sensor.

Light scattering methods such as Raman spectroscopy are known sensitive technique for detecting chemicals and biological agents. Due to technical difficulties, conventional Raman scattering sensors have so far limited applications. A major limitation in Raman spectroscopy is that the Raman scattering signals from trace chemicals tend to be very weak. Many attempts have been made to increase Raman scattering intensity. Such efforts, however, have not been able to deliver Raman spectroscopy-based detectors for practical and economical applications, despite urgent needs in many fields of applications such as antiterrorism, forensic analysis, disease diagnosis and prevention, industrial process monitoring, environmental cleaning up and monitoring, food inspection, anti-counterfeiting, and drug quality control.

Therefore, a need exists to provide effective and practical spectroscopy-based detectors for detecting trace amount of chemical or biological substances.

SUMMARY

In one aspect, the present invention relates to a method for detecting a chemical or biological substance. The method includes introducing a sample material into a sample solution containing nano particles; illuminating the sample solution containing the sample material and the nano particles by a laser beam; collecting light scattered by the sample material and the nano particles in the sample solution; obtaining a Raman spectrum from the light scattered by the sample material and the nano particles in the sample solution; determining the existence of a spectral signature associated with a chemical or biological substance around a predetermined wavelength in the Raman spectrum; and identifying the chemical or biological substance in the sample material based on the spectral signature in the Raman spectrum.

In another aspect, the present invention relates to a method for detecting a chemical or biological substance. The method includes introducing a sample material into a sample solution containing nano particles having an average dimension in a range from about 5 nm to about 500 nm, wherein the nano particles have a size distribution characterized by an average dimension and a width, wherein the ratio of the width to the average dimension is in a range from about 0.01 to about 3, wherein the nano particles comprise a magnetic or ferromagnetic material; illuminating the sample solution containing the sample material and the nano particles by a laser beam; collecting light scattered by the sample material and the nano particles in the sample solution; obtaining a Raman spectrum from the light scattered by the sample material and the nano particles in the sample solution; determining the existence of a spectral signature associated with a chemical or biological substance around a predetermined wavelength in the Raman spectrum; and identifying the chemical or biological substance in the sample material based on the spectral signature in the Raman spectrum.

In another aspect, the present invention relates to a method for detecting a chemical or biological substance. The method includes introducing a sample material into a sample solution, wherein the sample solution comprises nano particles having an average dimension in a range from about 5 nm to about 500 nm, wherein the nano particles have a size distribution characterized by an average dimension and a width, wherein the ratio of the width to the average dimension is in a range from about 0.01 to about 3; introducing an ionic material comprising multi-valence ions into the sample solution; illuminating the sample solution containing the sample material and the nano particles by a laser beam; collecting light scattered by the sample material and the nano particles in the sample solution; obtaining a Raman spectrum from the light scattered by the sample material and the nano particles in the sample solution; determining the existence of a spectral signature associated with a chemical or biological substance around a predetermined wavelength in the Raman spectrum; and identifying the chemical or biological substance in the sample material based on the spectral signature in the Raman spectrum.

In another aspect, the present invention relates to a method for detecting an ingredient in a food product. The method includes establishing a spectral signature in a Raman spectrum obtained from a chemical substance; allowing a food sample solution obtained from a food product to come to contact with a first nano-scale surface structure in a first sensor, wherein the first sensor comprises a substrate, wherein the nano-scale surface structure comprises a plurality of columns over the substrate or a plurality of holes in the substrate; illuminating the food sample solution and the first nano-scale surface structure on the first sensor by a laser beam; scattering the laser beam by the food sample solution and the first nano-scale surface structure to produce a scattered light; obtaining a first Raman spectrum from the scattered light using a spectral analyzer; and identifying the spectral signature in the first Raman spectrum to determine the existence of the chemical substance in the food product.

In another aspect, the present invention relates to a method for detecting an ingredient in a food product. The method includes allowing a reference sample solution containing the chemical substance to come to contact with a first nano-scale surface structure in a first sensor; obtaining a first Raman spectrum from the reference solution and the nano surface to establish a spectral signature in the first Raman spectrum for the chemical substance; allowing a food sample solution obtained from a food product to come to contact with a second nano-scale surface structure in a second sensor; illuminating the food sample solution and the second nano-scale surface structure on the second sensor by a laser beam; scattering the laser beam by the food sample solution and the second nano-scale surface structure to produce a scattered light; obtaining a second Raman spectrum from the scattered light using a spectral analyzer; and identifying the spectral signature in the second Raman spectrum to determine the existence of the chemical substance in the food product.

In another aspect, the present invention relates to a method for detecting an ingredient in a food product. The method includes allowing a reference sample solution containing the chemical substance to come to contact with a first nano-scale surface structure in a first sensor, wherein the first nano-scale surface structure includes a plurality of nano particles on a surface of the first sensor, or a plurality of columns or holes having an average neighboring distance in a range from 10 nanometers to 1000 nanometers; obtaining a first Raman spectrum from the reference solution and the nano surface to establish a spectral signature around a predetermined wavelength in the first Raman spectrum for the chemical substance, wherein the spectral signature includes at least one spectral peak around the predetermined wavelength in the first Raman spectrum; allowing a food sample solution obtained from a food product to come to contact with a second nano-scale surface structure in a second sensor, wherein the first sensor and the second sensor have substantially the same nano surface structures; illuminating the food sample solution and the second nano-scale surface structure on the second sensor by a laser beam; scattering the laser beam by the food sample solution and the second nano-scale surface structure to produce a scattered light; obtaining a second Raman spectrum from the scattered light using a spectral analyzer; identifying the spectral signature around the predetermined wavelength in the second Raman spectrum to determine the existence of the chemical substance in the food product, wherein the step of identifying comprises determining if the spectral peak in the Raman spectrum or a signal-to-noise ratio for the spectral peak is above a pre-determined threshold value; and positively identifying the chemical substance if the spectral peak or the signal-to-noise ratio is above the pre-determined threshold value.

Implementations of the system may include one or more of the following. The method can further include: after the step of introducing, allowing molecules of the sample material to adsorb to the nano particles. The nano particles can include a magnetic or ferromagnetic material. The nano particles comprise a material selected from a group consisting of iron, cobalt, and nickel. The method can further include applying an electrical field, a magnetic field, or an electromagnetic field to the sample solution during at least a portion of the step of collecting. The electrical field, the magnetic field, or the electro-magnetic field is static or alternating. The nano particles comprise a material selected from a group consisting of a metal, an oxide material, silicon, a polymeric material, and a combination thereof. The nano particles comprise a material selected from a group consisting of titanium oxide, silicon oxide, and zinc oxide. The nano particles comprise a material selected from a group consisting of Al, Ag, Au, Cu, Fe, Co, Ni, Cr, Zn, Sn, Pd, Pt, and a combination thereof. The nano particles have an average dimension in a range from about 1 nm to about 10,000 nm. The nano particles can have an average dimension in a range from about 5 nm to about 500 nm. The nano particles can have a size distribution characterized by an average dimension and a width, wherein the ratio of the width to the average dimension is in a range from about 0.01 to about 3. The sample solution can include multi-valence ions. The method can further include introducing an ionic material into the sample solution, wherein the ionic material comprises an ion selected from a group consisting of $Na^+$, $K^+$, $Li^+$, $Ca^{++}$, $Ba^{++}$, $Sr^{++}$, $Mg^{++}$, $Mn^{++}$, $Al^{+++}$, $Zn^{++}$, $Sn^{++}$, and $Sn^{++++}$, $F^-$, $Cl^-$, $Br^-$, and $I^-$. The sample solution can have an ionic concentration from about 10 µM to a saturated level. The spectral signature can include at least one spectral peak around the predetermined wavelength in the Raman spectrum, the method further comprising determining a concentration of the chemical or biological substance using the spectral signature if the chemical or biological substance is determined to exist in the sample material. The sample material can be extracted from a food product. The food product can include dairy products, candies, cookies, drinks, alcohol, meat, seafood, tea, fresh or canned vegetables, fruits, grain products, cereals, corn chips, potato chips, or protein containing food. The dairy products can include milk, milk powders, cheese, cheese-containing cakes, yogurts, ice creams, milk containing candies, or cookies. The product can include a dairy product, wherein the chemical or biological substance includes melamine and melamine cyanurate, wherein the spectral signature comprises one or more of spectral peaks around 678 $cm^{-1}$, 698 $cm^{-1}$, or 712 $cm^-$, or around 1648 $cm^{-1}$. The chemical or biological substance can include melamine, sodium cyclamate, sodium cyclohexyl-sulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, or enorfloxacin. The sample material can include a body fluid obtained from a person, the method further comprising: diagnosing a disease in the person based on the spectral signature determined in the Raman spectrum. The body fluid can include blood, saliva, urine, serum, tear, sweat, stomach fluid, sperm, and a secrete body fluid. The disease can be selected from the group consisting of lung cancer, breast cancer, stomach cancer, liver cirrhosis, a failing kidney, ulcer cancer, ovarian cancer, uterus cancer, cervix cancer, oral cancer, esophageal cancer, thyroid cancer, larynx cancer, leukemia, colon cancer, bladder cancer, prostate cancer, bronchus cancer, pancreas cancer, head cancer, neck cancer, skin cancer, HIV (virus), diabetes, smoking status, and drug addiction. The disease can include an illicit use of a drug selected from a group consisting of methamphetamine, cocaine, caffeine, morphine, codeine, amphetamine, ephedrine, papaverine, narcotine, and MDMA.

Embodiments may include one or more of the following advantages. The disclosed systems and methods provide simple and non-invasive approach to detect a disease in a patient. The disclosed systems are portable and easy to operate, and are thus ideal for being used for early disease prevention, and in-field drug usage screening. The disclosed systems and methods are suitable for early detect and diagnosis. The disclosed systems and methods also have short testing cycle time, and can therefore be very helpful for monitoring progresses in the treatment of diseases and drug use. The disclosed systems and methods can detect a wide range of disease such as oral cancer, breast cancer, lung cancer, stomach cancer, liver cirrhosis, a failing kidney, ulcer cancer, ovarian cancer, uterus cancer, cervical cancer, oral cancer, esophageal cancer, thyroid cancer, larynx cancer, leukemia, colon cancer, bladder cancer, prostate cancer, bronchus cancer, pancreas cancer, diabetes, HIV, smoking status as well as illicit drug use.

In another aspect, the present application provides convenient and application specific systems and methods for food inspection. Applications can include detection of harmful and un-authorized ingredients in food products (i.e., illegal food additives), and concentration of useful ingredients in food products. The disclosed systems and methods can implemented as portable devices and easy procedures to be used for food inspection in the filed with short test time.

In another general aspect, the disclosed system can detect trace biological or chemical substances using a light scattering probe and a chemical sensor. A solution containing the substance is transferred to the chemical sensor to allow molecules of the substance to be adsorbed on a nano structured surface on the chemical sensor. The substance is determined by illuminating laser light at the nano structured surface on the chemical sensor.

In another general aspect, the disclosed system can detect trace biological or chemical substance using a light scattering probe and a solution containing nano particles. The substance is dissolved in the solution allow molecules of the substance to be adsorbed on to the surfaces of the nano particles. A laser beam illuminates the solution directly. The light scattered by the nano particles is collected by the light scattering probe to determine the trace biological or chemical substances.

The disclosed light sensing systems and methods can be used in a wide range of applications. Examples of such applications include detection of explosives and biochemical weapons for homeland security, detection of illegal drugs, food inspection, disease diagnosis, product authentication, environmental monitoring, industrial hygiene, and industrial process monitoring.

BRIEF DESCRIPTION OF THE DRAWINGS

The following drawings, which are incorporated in and from a part of the specification, illustrate embodiments of the present invention and, together with the description, serve to explain the principles of the invention.

FIGS. 1A-1C illustrate exemplified configurations of trace chemical detection using Surface-Enhance Raman Scattering.

DETAILED DESCRIPTION

Figure 2:
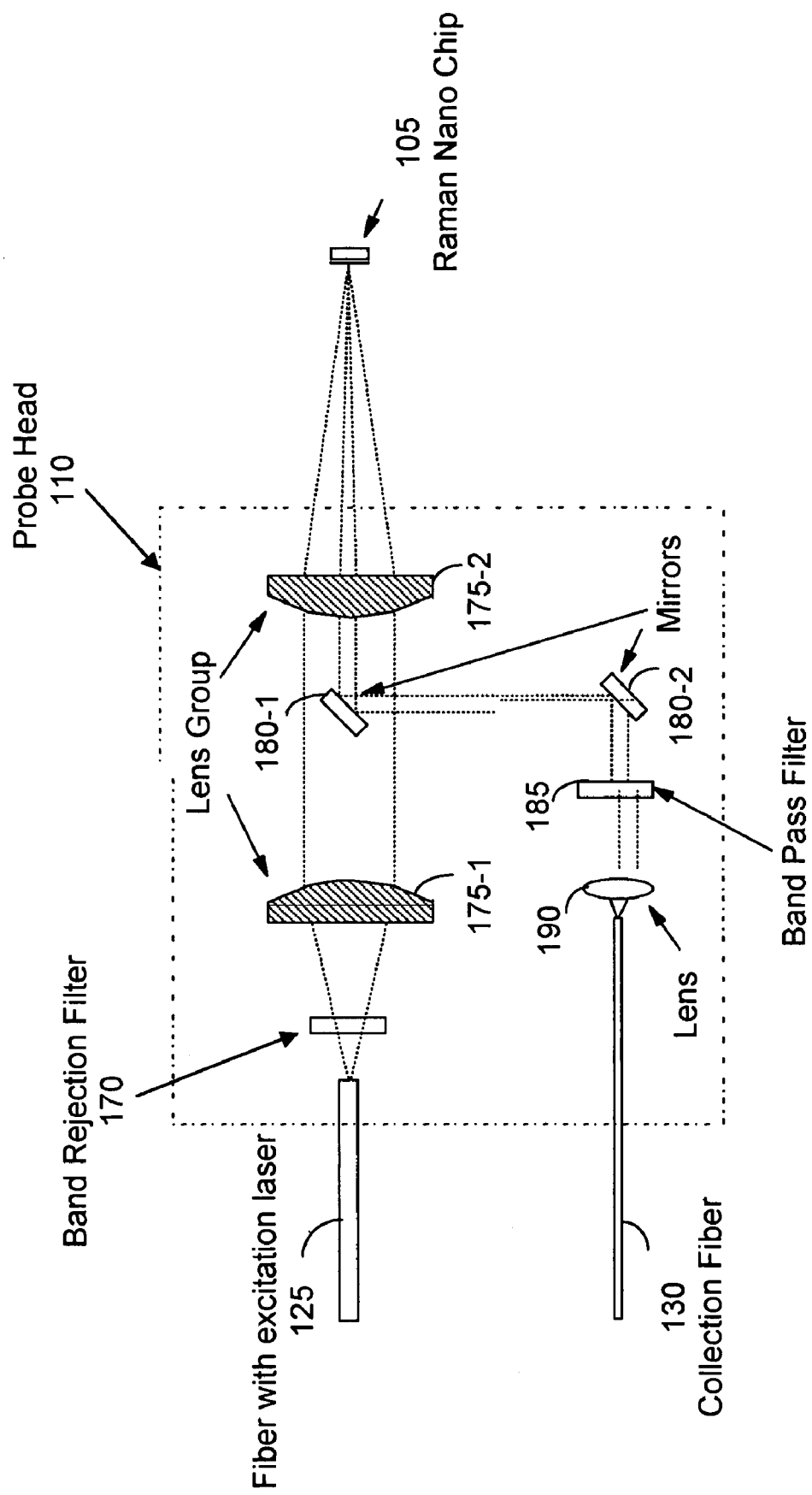
FIG. 2A illustrates an exemplified design of a probe head for Raman scattering probe.

Referring to FIG. 1A, a light scattering probe 100 includes a probe head 110 and a sensor 105. The sensor 105 includes a nano surface structure. The nano surface structure can include a plurality of nano rods 108, as shown in FIG. 1B, a plurality of nano holes, or other surface structures having dimensions at nanometer scale. In some embodiments, as described below, nano surface structures can be prepared by coating the surface of the sensor 105 of a solution containing a colloidal suspension of nano particles. The solution can be subsequently evaporated to deposit the nano particles on the surface.

Using the example of nano surface comprising nano rods 108, a sample fluid can be introduced to the nano rods 108 in the sensor 105. The sample fluid can include a body fluid obtained from a patient or an illicit drug user for disease diagnosis and drug use determination. Examples of the body fluid can include blood, saliva, urine, serum, tear, sweat, and stomach fluid. The sample can also include a food sample for detecting harmful or illegal additives in a food product to ensure food safety. Examples of good products include dairy products such as milk, milk powder (e.g., baby formula), cheese, yogurt, ice cream, milk containing candies, other milk contained food products, and protein-containing food products. The probe head 110 and the sensor 105 are enclosed in a probe assembly 120. The probe assembly 120 can be depressurized by a vacuum pump to reduce contamination of the sensing surfaces for foreign substance.

A laser beam emitted by a laser 141 is guided by an optical fiber 125 to illuminate the sensor 105, as shown in FIG. 1C. The probe head 110 is positioned adjacent to the sensor 105. In the present application, the term RamanNanoChip™ refers to a sensor comprising a nano-scale surface structure that is configured to adsorb molecules of a chemical, biological, or medical sample for detecting using a light scattering probe. The scattered light is collected by the probe head 110 and guided to a spectral analyzer 150 along by an optical fiber 130. A Raman spectrum of the scattered light is obtained by the spectral analyzer 150. The spectral signatures in the Raman spectrum are identified and to compared with database of spectral signatures for various molecules. An output signal can indicate identification of a disease when a threshold of certain molecules under detection is exceeded. In the present specification, the term "spectral signature" can refer to one or more spectral peaks, one or more spectral valleys, and other spectral shapes such as relative peak height, peak line width, peak shape, etc., that characterize one of more molecular bonds in a biological, medical, or chemical materials.

Referring to FIG. 2, the probe head 110 can receive a laser projection from an input laser fiber 125 to pass through a band ejection filter 170 to pass through a lens group 175-1 and 175-2 to project onto sensor 105. A scattering light is projected back to a group of mirrors 180-1 and 180-2 to pass through another band-pass filter 185 and a collimated lens to output from the collection fiber 130.

The trace chemicals or biological agents to be detected can be in the form of a gas, a liquid, a solid, a sol gel, and an aerosol. The molecules are adsorbed onto the nano surface or nano particles of the sensor. Such adsorbed molecules have much larger scattering cross section under laser beam illustration than that they are free form in gas, liquid, solid, sol gel, or aerosol. When laser beam illuminates the adsorbed molecules, Raman scattering spectrum of the molecules can be obtained. Targeted chemicals or biological agents can be identified since most molecules have their unique Raman spectral fingerprint signatures.

Figure 3A:
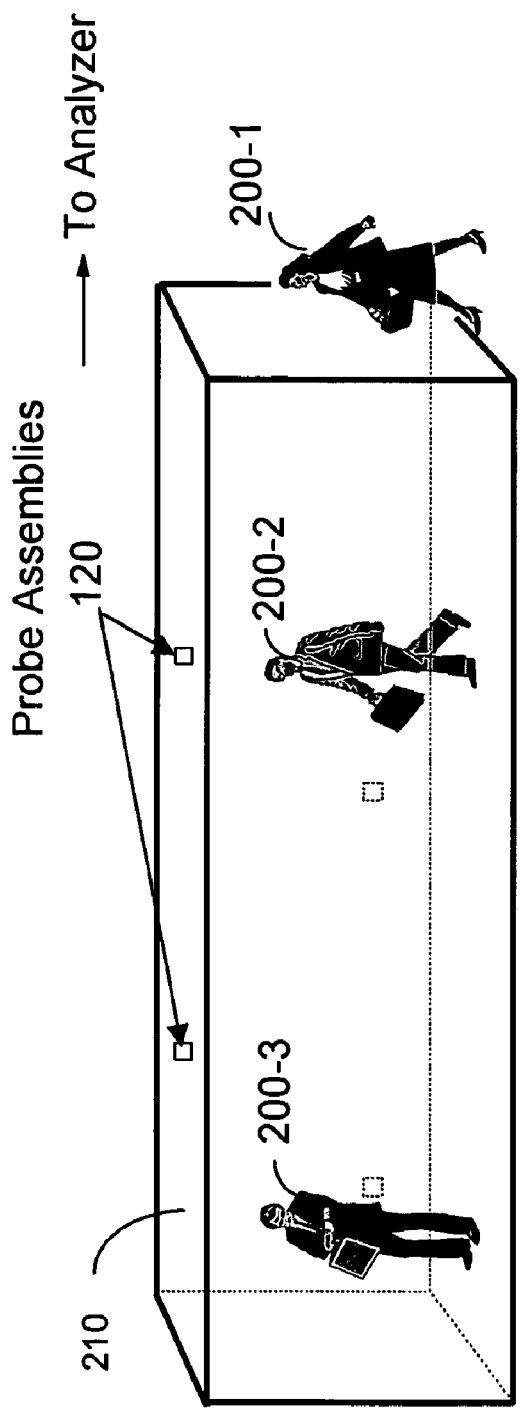
FIGS. 3A and 3B are schematic diagrams respectively showing inspections of passengers and luggage using a Raman scattering probe at an airport.

FIG. 3A is a schematic diagram to show a configuration of the Surface Enhance Raman Scattering application in safety of transportation and other places where a passenger screening is required to monitor passengers 200-1, 200-2, and 200-3. For passenger screening, the probe assembly 120 with embedded sensor 105 is placed in the passageway 210. The probes head 120 are connected by fibers to the spectral analyzer 150 in office near or far away from it. The probe head 120 is aligned to point to the sensing surface of a sensor 105 and they are packaged together. The passageway tunnel 210 can be forced ventilated and under little negative pressure and/or little higher temperature to increase evaporation of harmful materials. If a passenger, e.g., passenger 200-2, carrying explosive materials, harmful chemicals, chemical weapons, bio-chemical weapons, nuclear weapons or narcotic drugs, few molecules of such materials will volatilize into air that molecules are adsorbed onto the surface of a sensor through specially designed sample collection system. The Raman Spectrum will be recorded and compared with database in mainframe at office. As soon as the harmful materials are detected, early stage alarm signal will be triggered and appropriate security actions can be further processed.

Figure 3B:
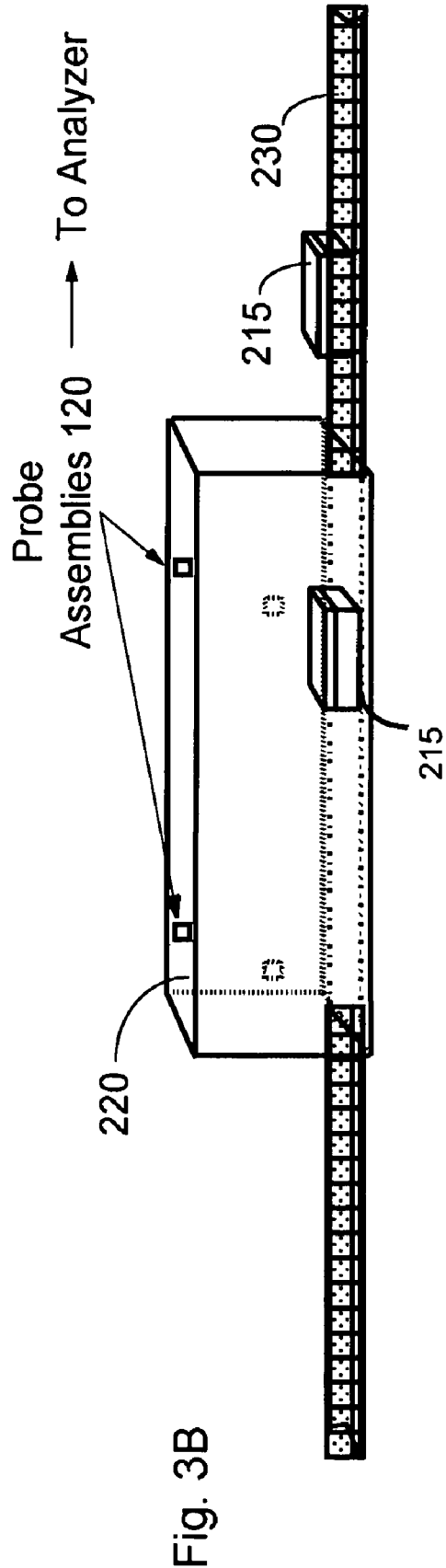

FIG. 3B is a diagram to show application implemented to monitor luggage 215 for freight transportation carried by a conveyer 230 to pass through cargo screening channel 220. The probe assembly 120 with embedded sensor 105 is placed around the cargo screen channel 220. The probes head 120 are connected with fibers to the spectral analyzer 150 in office near or far away from it. The probe head 120 is aligned to the surface of a sensor 105 and they are packaged together to detect any explosives, chemical or biochemical weapon, or harmful chemicals enclosed in the luggage 215. This configuration can be implemented in other applications such as mail stations, railway stations, custom inspection areas, traffic control zones, etc. This configuration can be easily implemented to detect gun powders or other explosives or hazardous materials.

Figure 4:
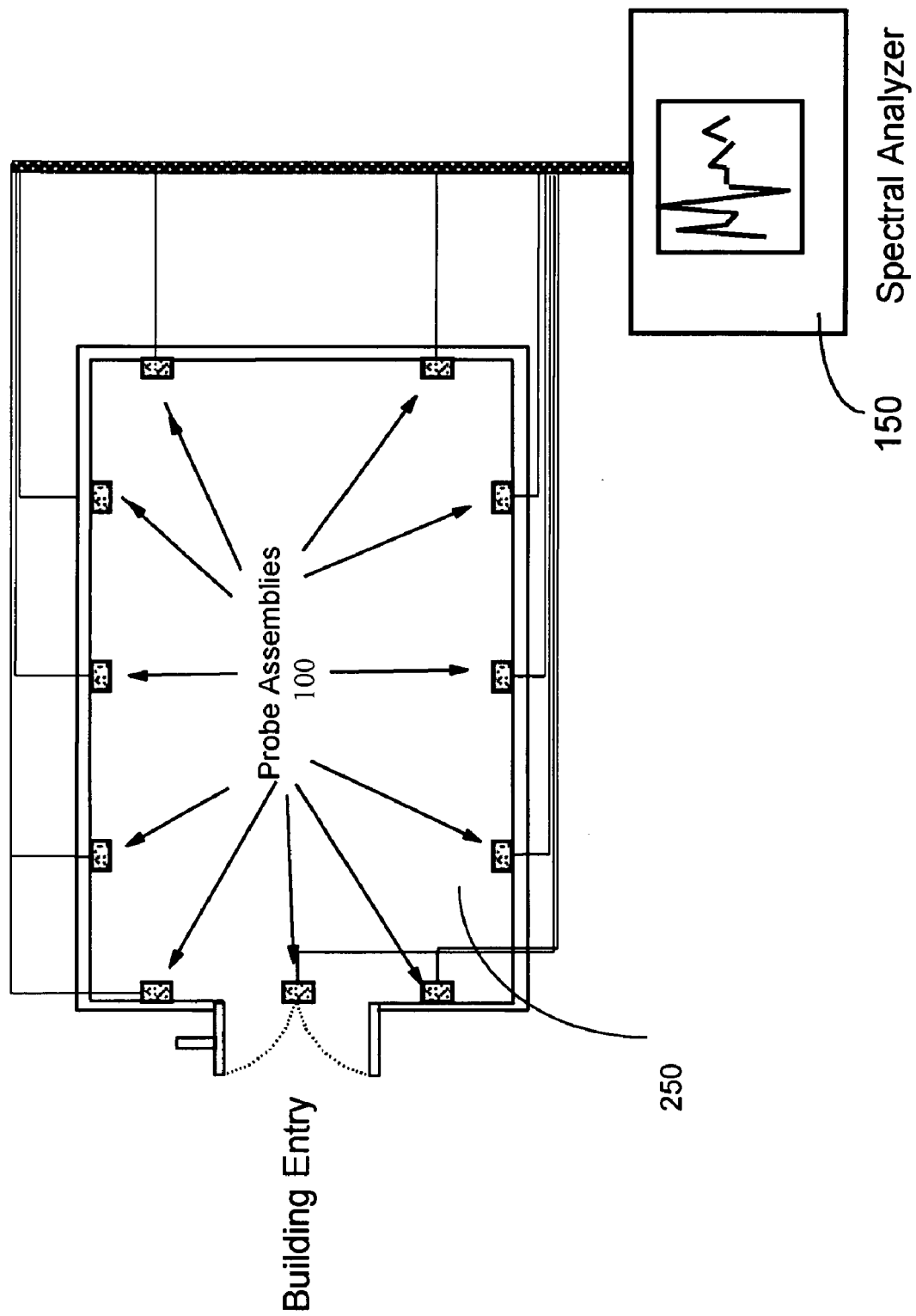
FIG. 4 is a schematic diagram showing safety monitoring in public building safety using a Raman scattering probe.

FIG. 4 is schematic diagram of Surface-Enhance Raman Scattering applications using a sensor in safety of public buildings 250 such as airport, railway or bus stations, ballpark buildings, Federal buildings, auditoriums, theaters, courthouses, and other public buildings. The light scattering probe 100 that includes probe head 120 combined with a sensor 10 are distributed in the public buildings or others protected areas. The light scattering probes 100 are applied to monitor many different molecular substances to provide earlier detection of any dangerous or harmful chemicals enter into the monitor areas. Particular examples of hazardous material monitoring include, but not limited to detection of explosive materials, chemical or biochemical weapons including anthrax, drugs, and so on.

Figure 5:
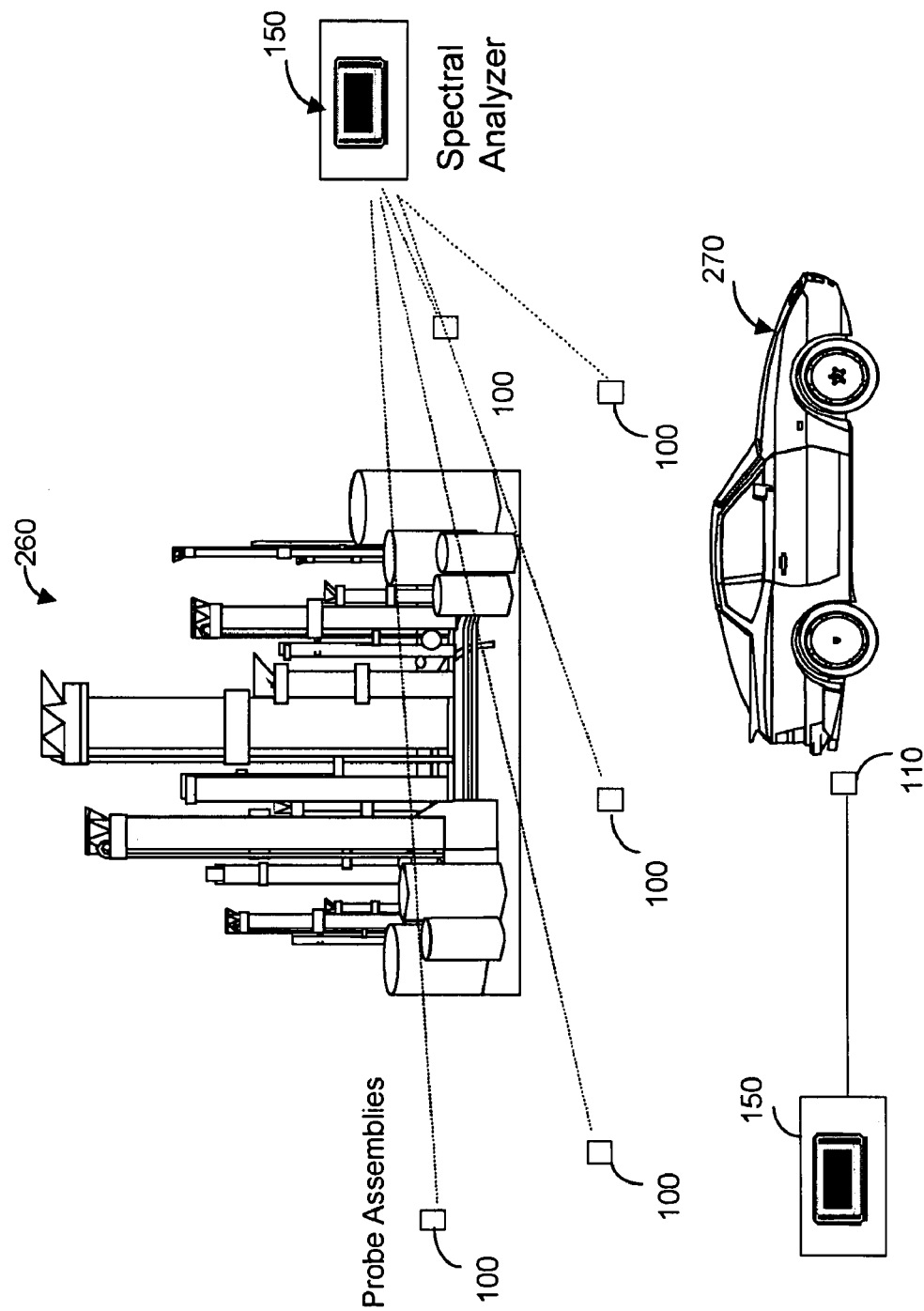
FIG. 5 is a schematic diagram showing environmental monitoring using a Raman scattering probe.

FIG. 5 is schematic diagram of applying the technology of Surface-Enhance Raman Scattering using a sensor to monitor harmful chemicals released into the environment. The light scattering probes 100 are distributed around potential pollution source, e.g., a factory 260 or around highway where great number of automobiles 270 pass through. The light scattering probes 100 distributed around the monitored areas generate Raman scattering light that is transmitted to a mainframe spectrum analyzer 150 to determine the contents and concentration of substance released into the environment. The monitoring sample can be, but not limited, soil, water, lake, river, seashore, well, plants, etc. This application can be extended to car exhausted gas detection and monitoring by placing the probe assembly near by car exhausting output.

Figure 6A:
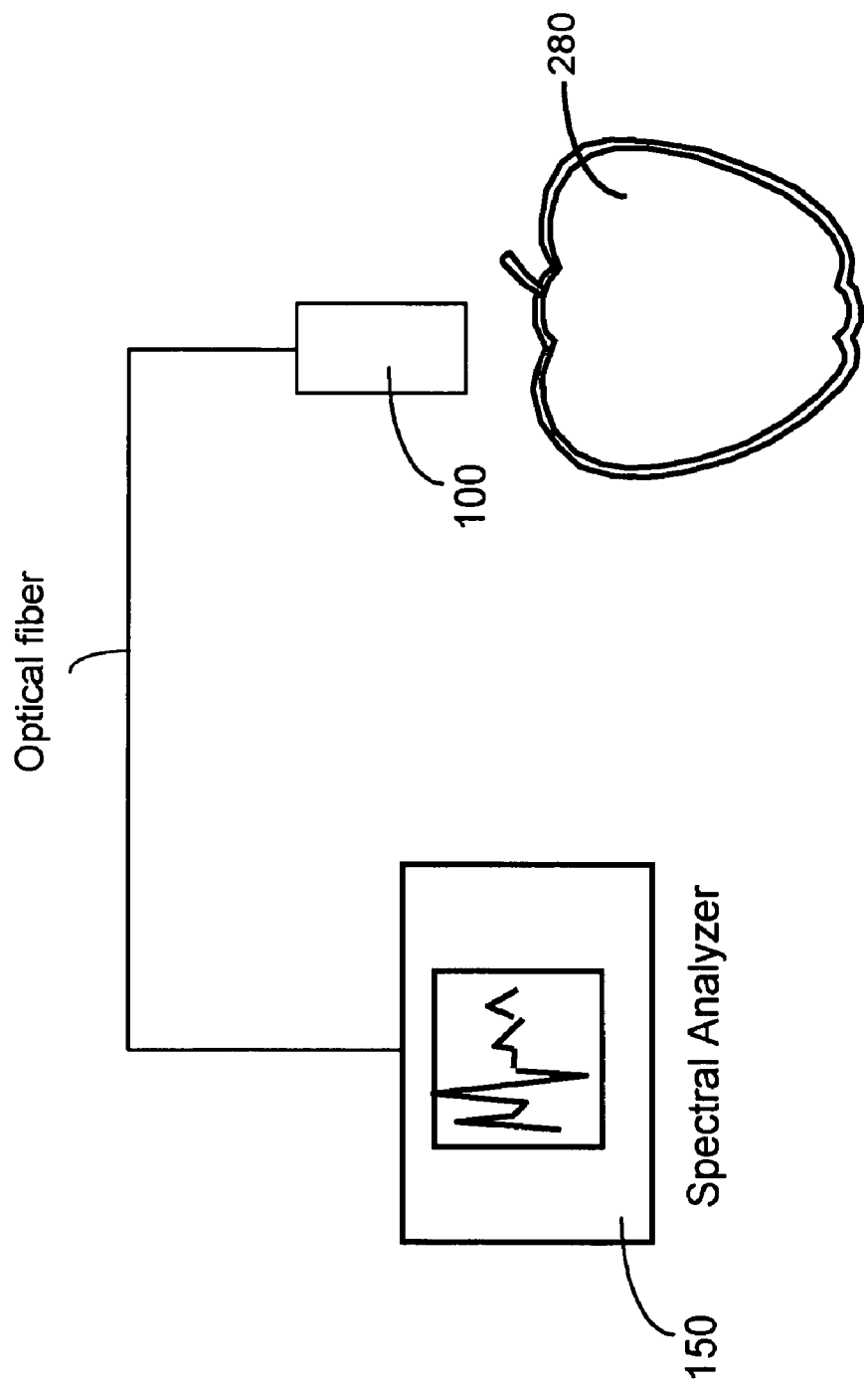
FIG. 6A is a schematic diagram showing inspection of food safety using a Raman scattering probe.

FIG. 6A is schematic diagram of applying the technology of Surface Enhance Raman Scattering using a sensor to monitor substances for inspecting quality and safety of foods. The light scattering probes 100 is placed close to a food item 280, i.e., an apple or different fruits, vegetables or other food items that could be contaminated through transportations, food processing, or even food growth process. The molecules of residue pesticide or other contaminations are drawn into the light scattering probe 100. A sensor is used to detect any suspect harmful chemicals contained in the food.

Figure 6B:
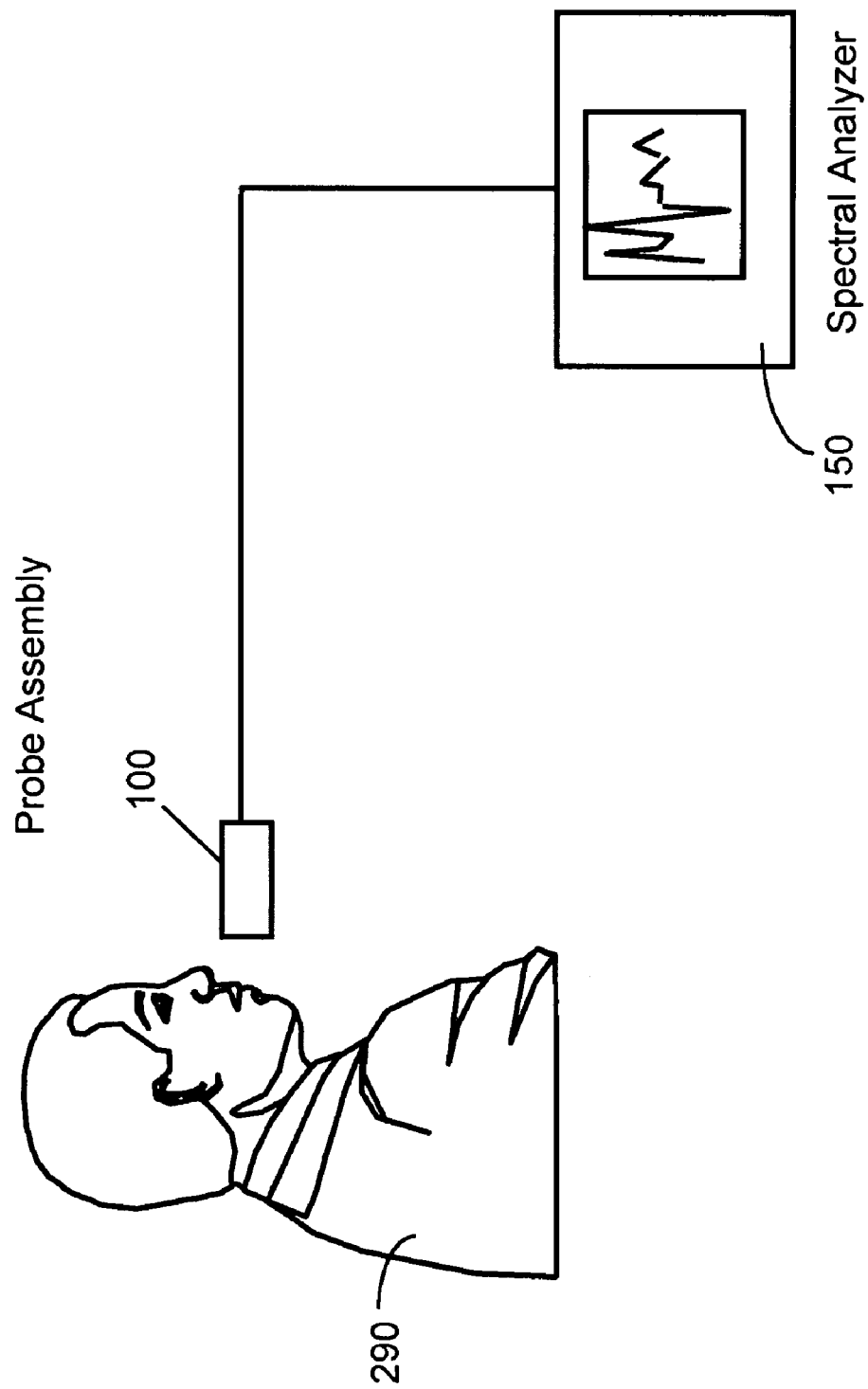
FIG. 6B is a schematic diagram showing disease diagnosis and biomedical detection using a Raman scattering probe.

FIG. 6B is schematic diagram of applying the technology of Surface Enhance Raman Scattering with or without using a sensor to monitor substances for early decease detection and diagnosis. The light scattering probe 100 is placed near a patient 290. Research result indicated that human breathed air have special chemicals contained, such as alkenes and benzene derivatives, if a person under screening is associated with disease, such as lung cancer. Raman sensing technology is able to fingerprint those chemicals in breath test to identify some special diseases such as cancers. The light scattering probe 100 is placed near the patient for carrying out a physical examination. The patient blows the outpoured breath-air to the light scattering probe 100. The sensor in probe assembly receives the inlet air for generating a Raman scattering light corresponding to the molecules contained in the airflow from the patient. The scattering lights are collected by probe head and sent to the spectral analyzer 150 to generate Raman spectrum. Breath test with Raman sensing technology is to make early disease diagnosis which disease includes, but not limited to lung cancer, breast cancer, stomach cancer, Liver cirrhosis, failing kidney, ulcer cancer, etc. In case of testing human body fluids, the fluid is dropped on a sensor manually, or Raman sensing device can be designed to connect to toilet for easy sample collection as smart toilet to timely monitor abnormal signals for disease and drug detection. This application also includes identifying and sorting protein, DNA and RNA. All testing samples in above applications can be placed in contact with a sensor to enhance the sensitivity and intensity of Raman scattering detections. The disclosed trace chemical detection using Raman light scattering can also be applied to other areas, including but not limited to identify Alzheimer's disease, non-invasively test glucose to monitor diabetes, non-invasive test carotenoids to monitor antioxidant status for early cancer screening purpose, and so on.

Figure 6C:
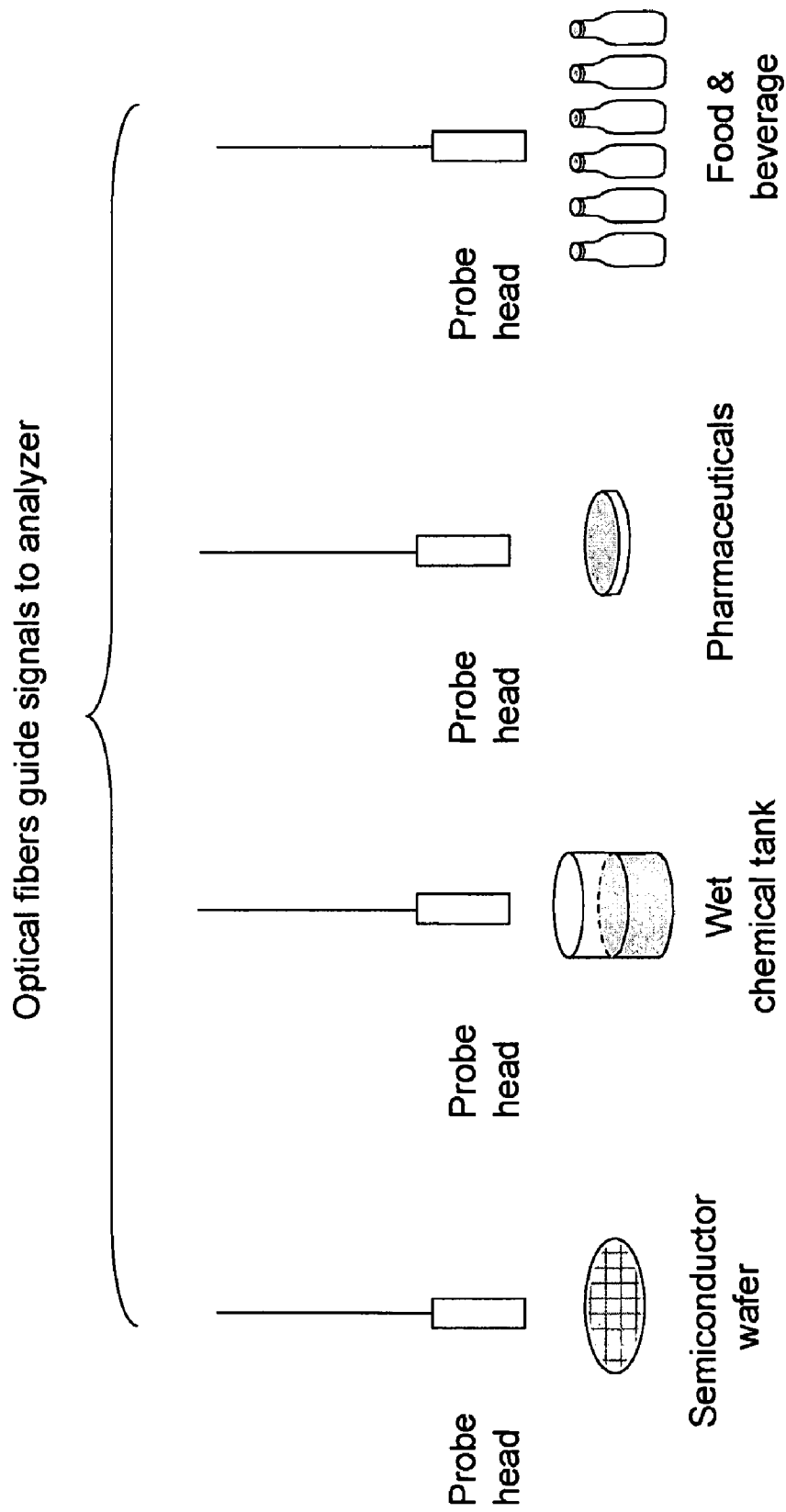
FIG. 6C is a schematic diagram showing manufacture quality control with and without a Raman scattering probe.

FIG. 6C is schematic diagram of Raman scattering application in industrial quality control with or without a sensor such as a RamanNanoChip™. The applications include, but are not limited to, the in-line monitoring wet chemical concentration in wet chemical process line, stand-off monitoring of sealed chemical tanks, remote trace chemical detection, semiconductor wafer defect evaluation, and monitoring of the food, fruit and vegetable storage, etc.

Figure 6D:
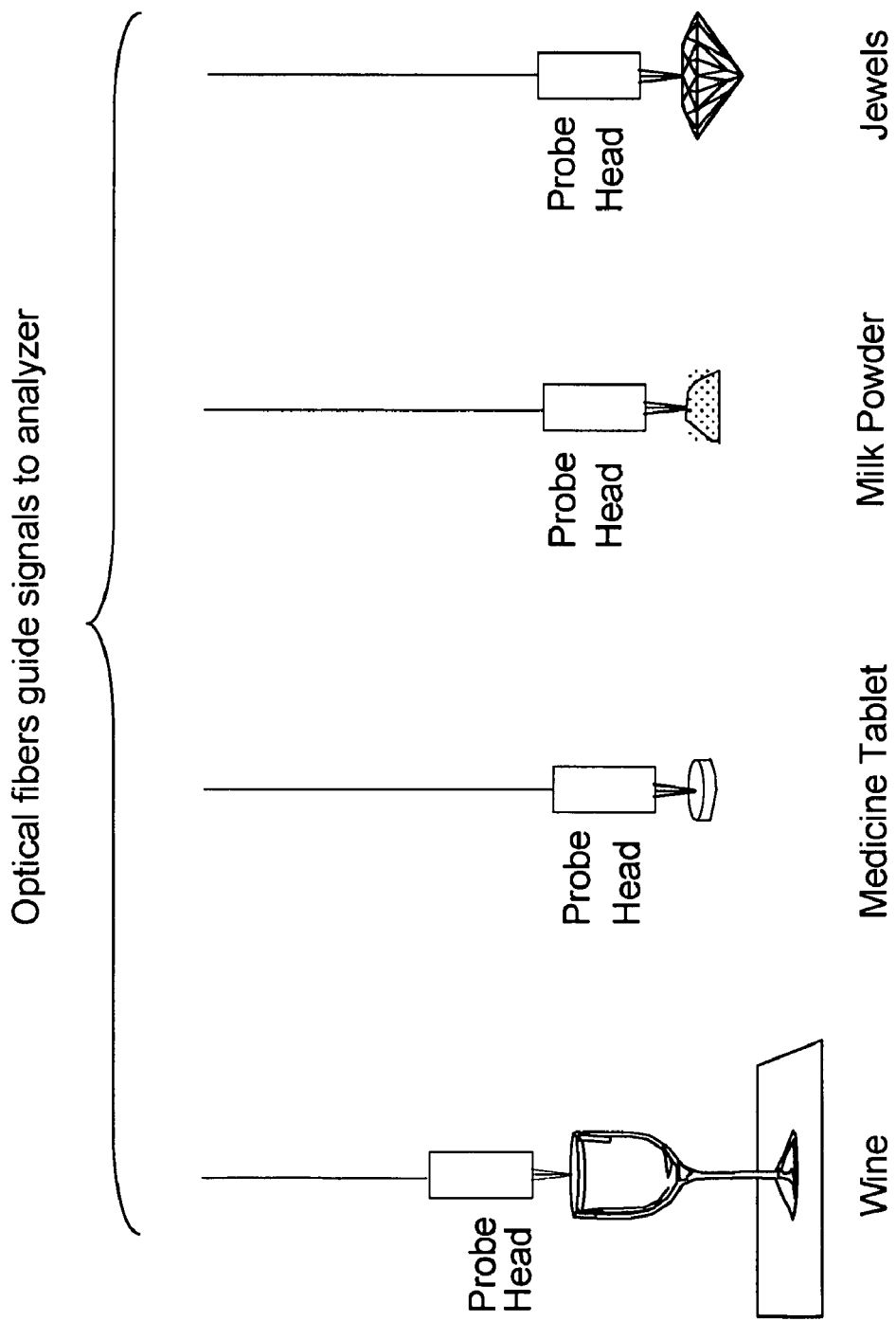
FIG. 6D is a schematic diagram showing detection of counterfeit merchandise, inspection of safety and quality food and beverages, and drug authentication using a Raman scattering probe.

FIG. 6D is schematic diagram of applying the technology of Surface Enhance Raman Scattering to identify and screen materials for counterfeit merchandise and food safety screening. The applications may include operations such as food, drug and medicine screening. In theses cases, a sensor may or may not be required. The excitation laser directly strikes on samples under test. With improvement of the whole system of Raman Spectroscope, new applications that might not be available previously are now become practical. The Raman Spectrum of scattering light from the tested materials shows characteristic contents thus provide clear indications whether there are illegal additives added to the commercial merchandises. The potential counterfeit merchandise such as milk-based powder, wine, and medical tablets may be placed under the Raman detector as materials under investigation and screen. The applications can be extended to authenticated signatures and currency bills by detecting false signature and false bills by generating Raman scattering spectrum of the signature and dollar bills and compare these spectrum with measurements obtained from authenticated signature and dollar bills.

Figure 7:
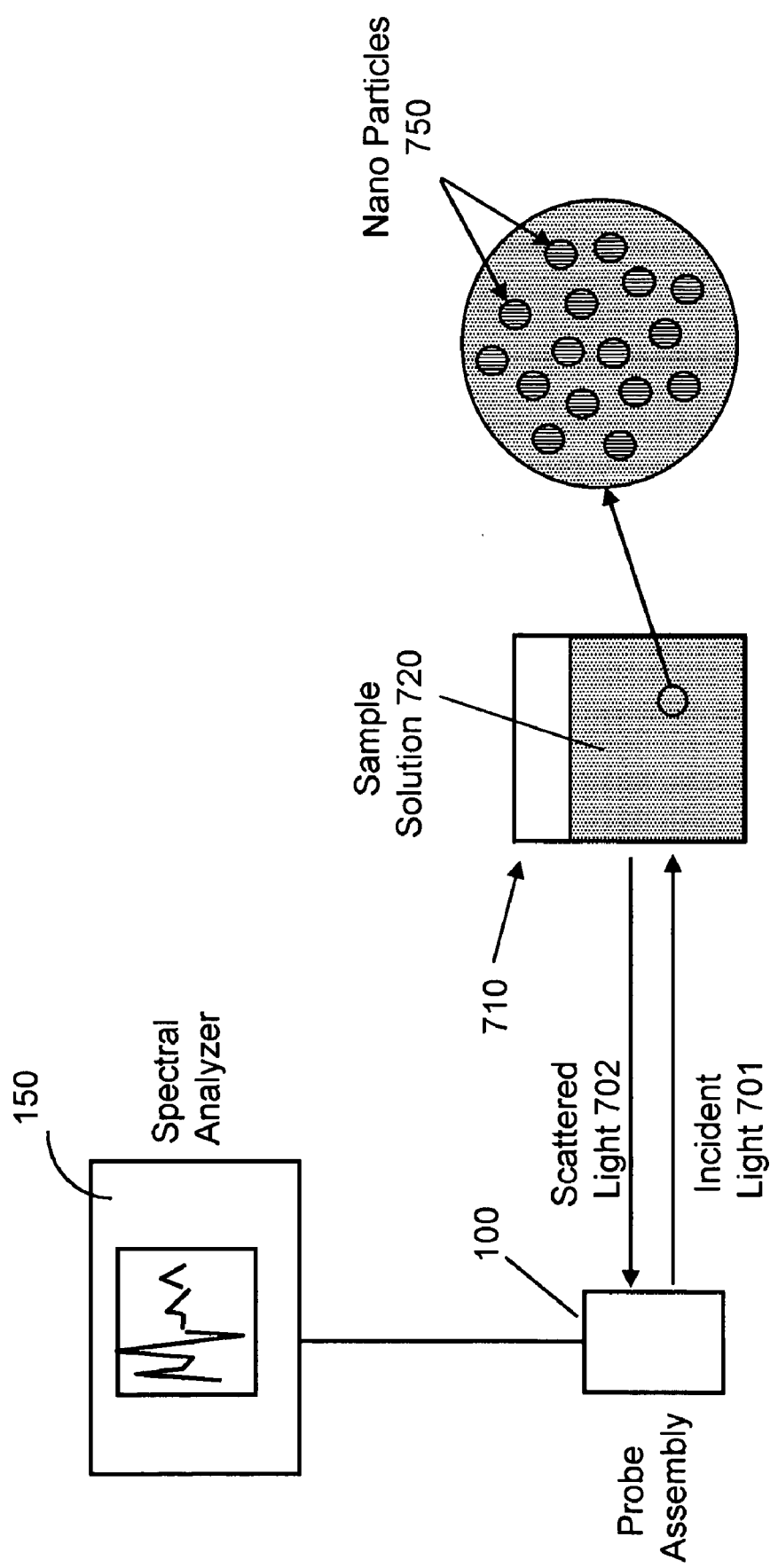
FIG. 7 is a schematic diagram showing a configuration for detecting trace chemical or biological substance using a solution containing nano particles and a light scattering probe.
Figure 8:
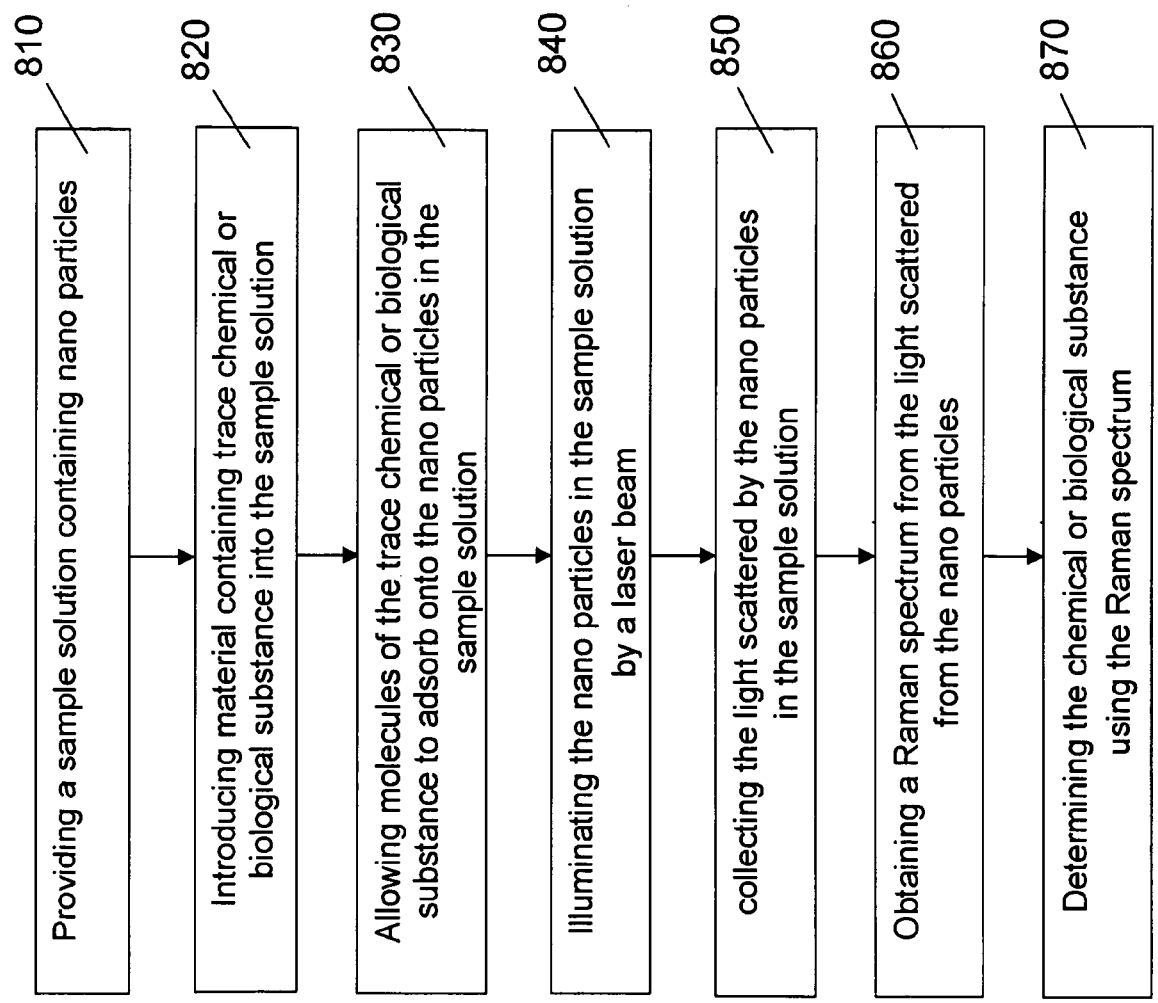
FIG. 8 is flow diagram for detecting trace chemical or biological substance using a solution containing nano particles and a light scattering probe.

In some embodiments, referring to FIGS. 7 and 8, a sample solution 720 is introduced into a container 710 (step 810). The container 710 can be an optical vial, a beaker, or a transparent test tube, etc. The sample solution 720 also contains nano particles 750 or carbon nao tubes. The nano particles 750 can exist in the form of a colloidal suspension in the sample solution 720. A sample material containing the chemical or biological substance is introduced into the sample solution 710 (step 820). The sample material can exist in a solid, a liquid, an aerosol, a sol gel, or a gas form. The sample material is dissolved in the sample solution 720 to allow molecules of the chemical or biological substance to adsorb on surfaces of the nano particles 750 (step 830). A light scattering probe 100 emits an incident light 701 (such as a laser beam) to illuminate the nano particles 750 and the chemical or biological substance in the sample solution 720 (step 840). Scattered light 702 from the nano particles 750 and the chemical or biological substance is collected by the probe assembly 100 (step 850). The output signal from the probe assembly is analyzed by the spectral analyzer 150. As shown in more detail in the examples below, a Raman spectrum is obtained from the scattered light (step 860). Spectral signature(s) in the Raman spectrum can be used to determine the trace chemical or biological substance adsorbed to the nano particles (step 870).

In one aspect of the present disclosure, material compositions of the nano particles 750 in the sample solution 720 are prepared to enhance the intensity of the scattered light 702 and Raman spectral signal from the nano particles. For example, the nano particles 750 include metallic materials such as Al, Ag, Au, Cu, Fe, Co, Ni, Cr, Zn, Sn, Pd, Pt, and their alloys, oxide materials such as titanium oxide, silicon oxide, zinc oxide, etc, silicon, and polymeric materials. The nano particles 750 can be charged in the sample solution 720 to assist the separation between the nano particles and the formation of a colloidal suspension. The nano particles 750 can also include polymers tethered to the particle surfaces to help repel each other in the sample solution 750.

In some embodiments, the nano particles 750 can include carbon nano tubes. The diameters of the carbon nano tubes can be from 0.3 nm to 100 nm. Their lengths can be from 5 nm to multiple millimeters. The length-to-diameter ratio of the carbon nano tubes can be as high as 50 million. The carbon nano tubes can have single-walls or multiple walls. The carbon nano tubes can be in the form of Fullerite, a torus, nanobuds, and nanoflowers.

In the presently disclosed systems and methods, when the carbon nano tubes can be placed the sample solution 720 to form a suspension of nano particles in which the sample material is added. The carbon nano tubes can also be introduced on a substantially flat surface or a surface already formed with nano structures. A sample material is then introduced to such a surface containing the nano carbon tubes. In either cases, a light optical beam (such as a laser beam) is directed to illuminate the nano carbon tubes and the sample material. Enhanced localized electromagnetic filed can assist charge transfer between molecules of the targeted chemical or biological substances, which results in enhanced Raman spectral signal.

In another aspect of the present disclosure, the nano particles 750 can be made of a magnetic or ferromagnetic material such as Iron (Fe), Cobalt (Co), and Nickel (Ni), or Fe, Co Ni contained compounds, such as alloy or oxide of Fe, Co, Ni, which can enhance the Raman spectral signal by applying an electrical field, a magnetic field, or an electromagnetic field to the sample solution 750. The electrical field, the magnetic field, or the electromagnetic field can be static or alternating.

In another aspect of the present disclosure, the sample solution 720 can include a mixture of nano particles of different material compositions. For example, the nano particles can include a mixture of silicon nano or micro-particles and metallic nano particles, or a mixture of silicon nano or micro-particles and polymeric nano particles, or a mixture of silicon nano or micro-particles, metallic nano particle, metallic oxide nano particles, and polymeric nano particles. Raman signal intensity can be enhanced by mixture compositions.

In another aspect of the present disclosure, the solvent in the sample solution 720 is also designed to enhance the light scattering intensity from the nano particles. It was found that ions and especially multi-valence ions can significantly enhance the signal intensity of the Raman signal. An ionic material can thus be added to the sample solution 720. Examples of ions that the ionic material carries to the sample solution 720 can include $Na^+$, $K^+$, $Li^+$, $Ca^{++}$, $Ba^{++}$, $Sr^{++}$, $Mg^{++}$, $Mn^{++}$, $Al^{+++}$, $Zn^{++}$, $Sn^{++}$, $Sn^{++++}$, $F^-$, $Cl^-$, $Br^-$, and $I^-$, and so on. The ions can have mono charge or preferably double or high charges in the sample solution 720. The ions can have positive or negative charges. The sample solution 720 can have an ionic compound, including but not limited to LiF, NaF, NaCl, KCl, KI, etc. The ionic concentration can be in a range from 10 µM to saturated level.

Figure 9A:
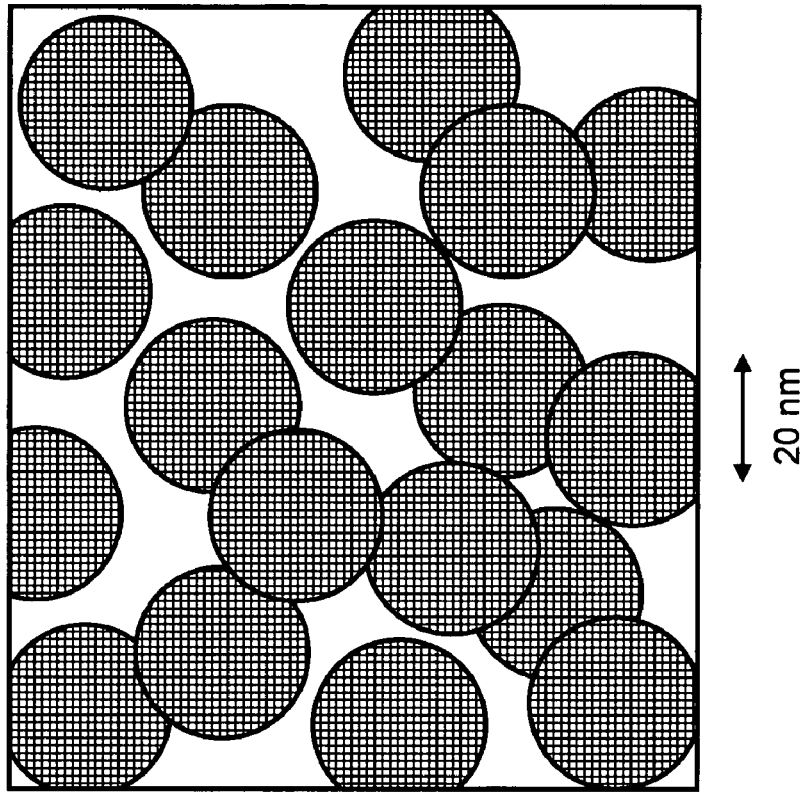
FIG. 9A is an exemplified micrograph of the nano particles shown in FIG. 7 using scanning electron microscope.
Figure 9A:
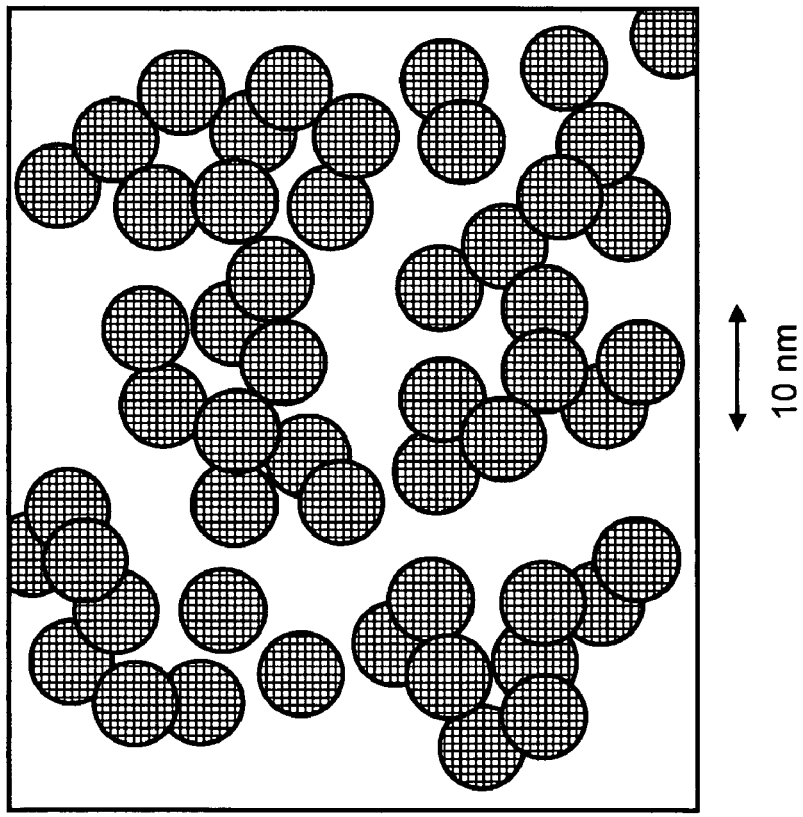
Figure 9B:
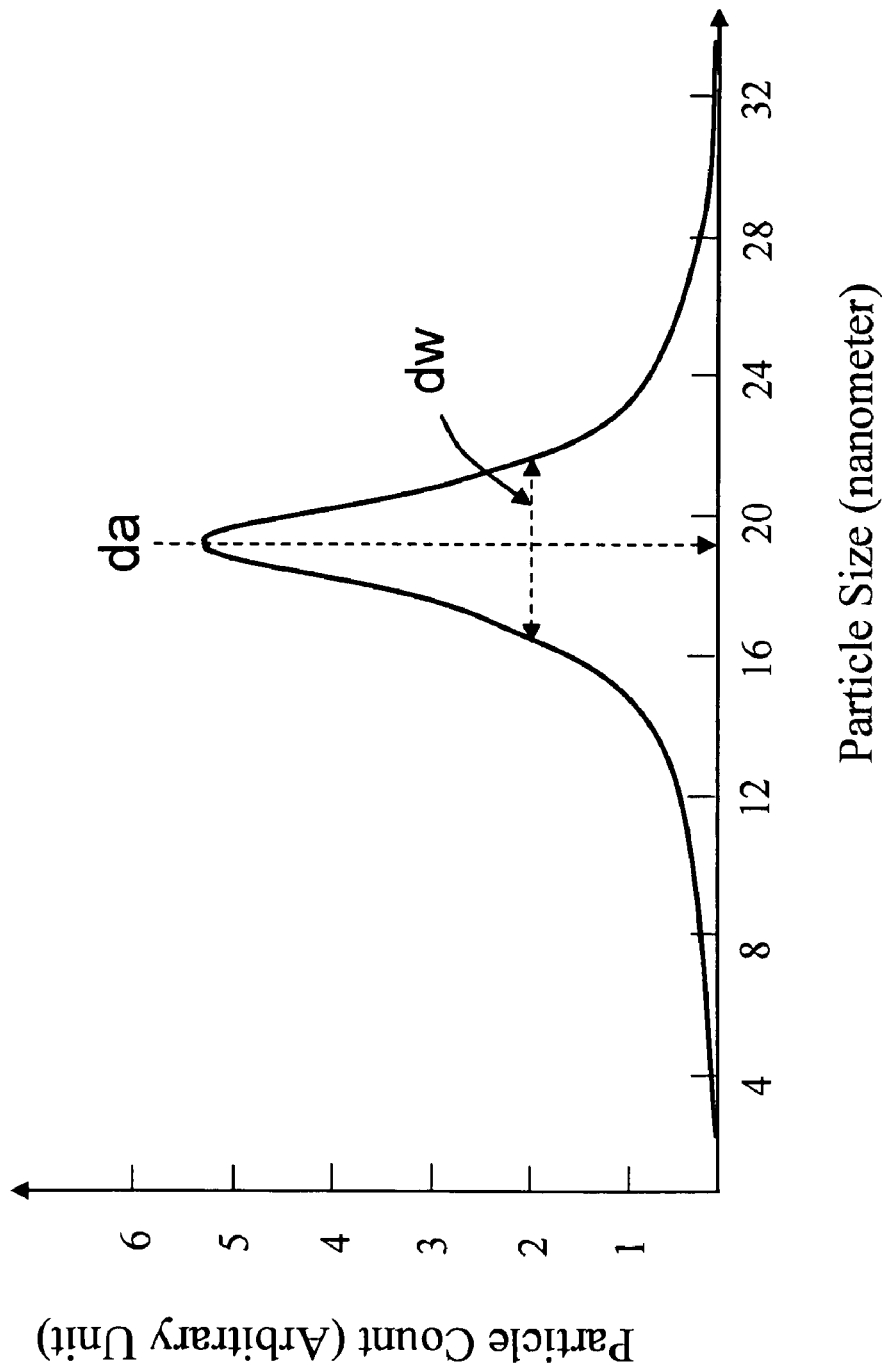
FIG. 9B is an exemplified size distribution of the nano particles in the solution shown in FIG. 7.
Figure 10:
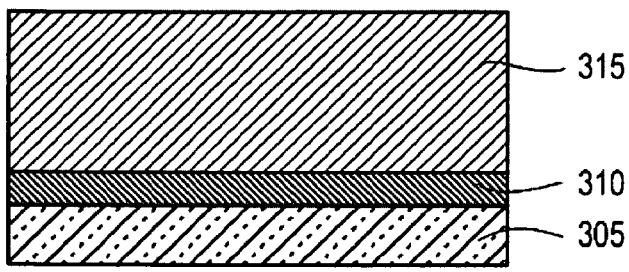
FIG. 10 is a cross-sectional view of a multi-layer layer structure to be used for fabricating a nano-structure.
Figure 11B:
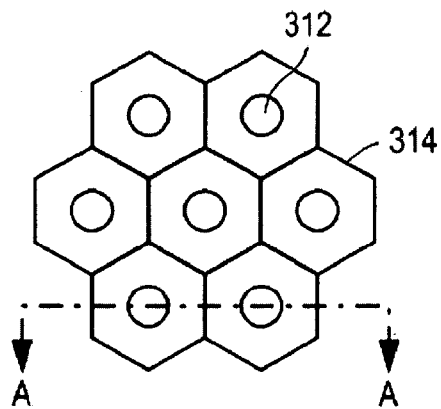
FIG. 11B is a top view of the multi-layer layer structure of FIG. 11A.
Figure 11A:
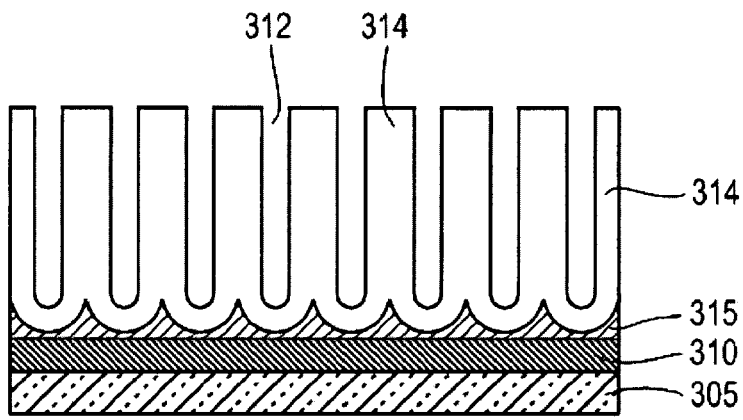
FIG. 11A is a cross-sectional view showing the formation of holes by anodization in the multi-layer layer structure of FIG. 10.
Figure 11C:
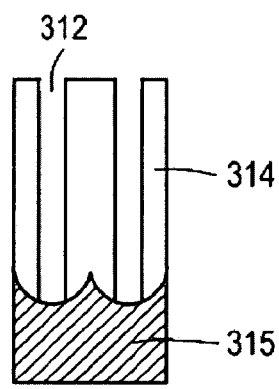
FIG. 11C is a cross-sectional view of the multi-layer layer structure along the line A-A in FIG. 11B.
Figure 12:
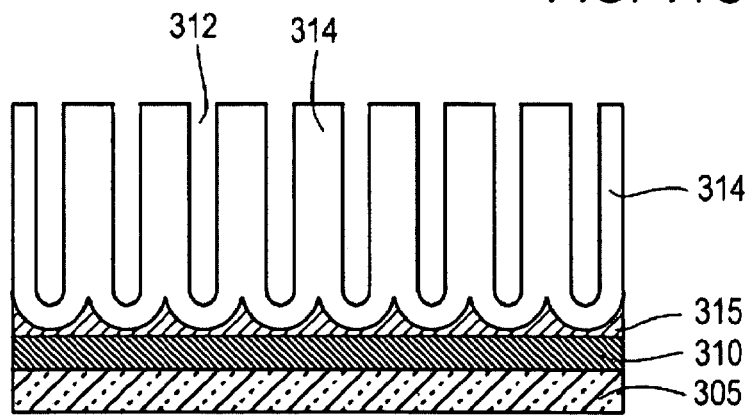
FIG. 12 is a cross-sectional view of the nano-structure formed on the multi-layer layer structure after a wet chemical etch or chemical mechanical polishing (CMP).

The nano particles 750, as shown in FIG. 9A, can exist in round or irregular shapes. The nano particles can be individually separated and have also group in clusters in the sample solution 720. The nano particles 750 can have a size distribution, as shown in FIG. 9B, which is characterized by an average particle dimension da and a width dw for the particle size distribution. The average particle dimension da can range from about 1 nm to about 10,000 nm, or from 2 nm to 500 nm. The ratio dw/da can range from about 0.01 to about 3, which defines a quite monodispersed distribution to a polydispersed particle distribution. The ratio dw/da can often range from about 0.03 to about 1.

In some embodiments, substance containing the trace chemical or biological substance can be introduced onto the surface of a chemical sensor, as shown in FIG. 1, from which an incident light can be scattered and a Raman spectrum can be obtained fro material determination. FIGS. 10 to 15 show a series of processing steps for fabricating a nano-structured noble metal surface on the chemical sensor (or sensor 105 in FIG. 1). A multi-layer structure 302 (FIG. 10) includes a substrate 305, a conductive layer 310, and an aluminum oxide layer 315. The substrate 305 can for example be n-type silicon flat wafer (3-8 Ω-cm) or oxidized (30-50 nm $SiO_2$) p-type silicon (5-10 mΩ-cm). The conductive layer 310 can include Ti and Ni and is deposited on the substrate 305 and can be electrically and thermally conductive. The thickness of the conductive layer 310 can be optimized to provide i) adhesion to a subsequently deposited noble metal film, such as Ag, or Au film, etc., ii) electrical conductive film to apply electrical bias to sensing surface in field application, iii) thermal conductive layer to apply lower temperature of sensing surface. The thickness of the conductive layer 310 can be typically controlled in the range of 100 Å-1,000 Å.

The aluminum layer 315 is deposited on the conductive layer 310. The aluminum layer 315 can have a purity of 99.999% and thickness in the range of 1.0-10.0 µm. The substrate 305, the conductive layer 310, and the aluminum oxide layer 315 are annealed at 400° C.-500° C. in a $N_2$ purged furnace for 2-5 hours to recrystallize the Al film. Anodization is then conducted to produce a porous structure in a form of porous aluminum oxide layer 315 as that shown in FIGS. 11A and 11B. A porous structure is formed on the aluminum oxide layer 315 wherein the porous structure includes a plurality of pores 312 surrounded by walls 314 with the cross section view along a horizontal line A-A shown in FIG. 11C. Then wet oxide etch process is carried out in FIG. 12 to remove both top porous $Al_2O_3$ layer and barrier layer. A second anodization is carried out to consume all Al metal so that the barrier layer and top porous $Al_2O_3$ layer are right above the conductive metal layer.

Figure 13:
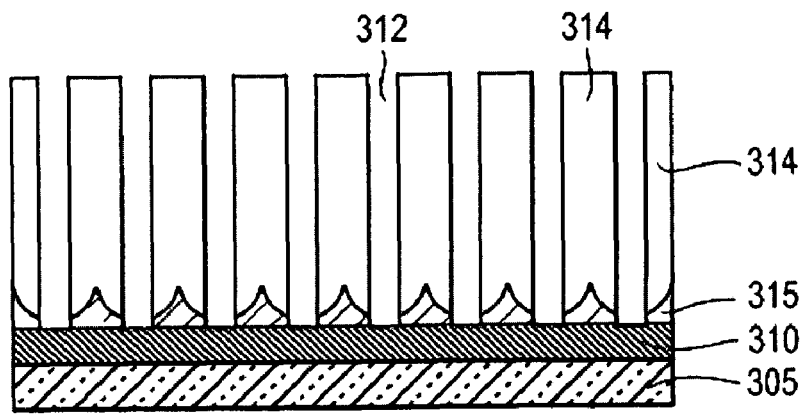
FIG. 13 is a cross-sectional view of the nano-structure formed on the multi-layer layer structure after the removal of the barrier layer at the bottom of the holes and etching down to the conducting layer.

In FIG. 13, an oxide etching is carried out to remove the barrier layer at the bottom of the pores and to widen the pore diameter. The wet etch process allows the pores 312 to extend downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) and the inter-pore distance (D) can depend on applied anodization voltage (V), current density (i) and the properties of the electrolyte, and the subsequent pore widening wet etch process.

Figure 14A:
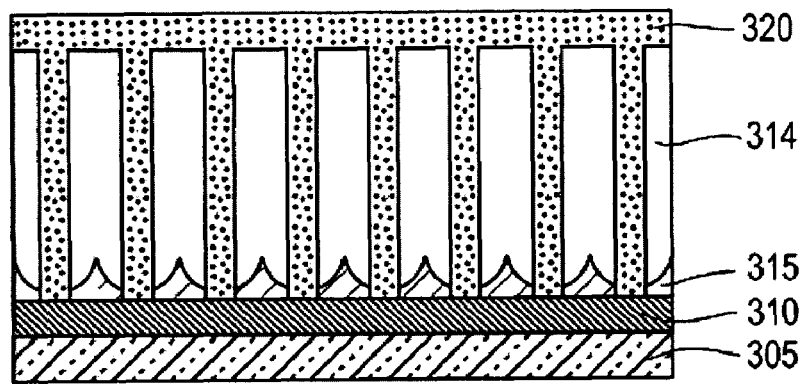
FIG. 14A is a cross-sectional view of the nano-structure formed on the multi-layer layer structure after the deposition of a noble metal.
Figure 14B:
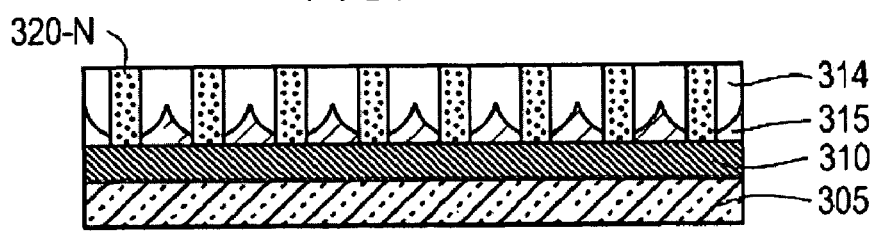
FIG. 14B is a cross-sectional view of the nano-structure formed on the multi-layer layer structure after the removal of the noble metal on the top layer.
Figure 15:
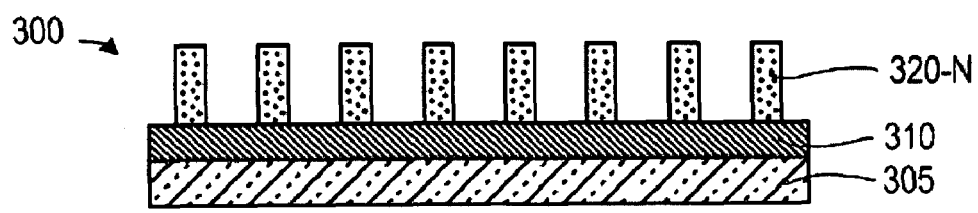
FIG. 15 is a cross-sectional view of the nano-structure formed on the multi-layer layer structure after the oxide layer is removed.

Referring to FIG. 14A, a noble metal such as Ag is deposited on the porous layer 315 to fill the pores 312 and to form a layer 320. The layer 320 can be formed by PVD process or electroplating. In FIG. 14B, a layer of the noble metal 320 is removed while leaving the noble metal 320-N in the pores 312. Another wet metal etch or CMP process is applied further control height of the noble metal 320-N filling the pores. In FIG. 15, the aluminum oxide 315 and the residue aluminum film 315-AL at the bottom of the porous aluminum layer 315 are removed to form a nano-structured surface 300 comprising an array of nano rods 320-N.

The nano rods 320-N are substantially straight and are perpendicular to the substrate 305 and the conductive layer 310. The nano rods 320-N can have substantially the same or similar widths. The neighboring nano rods 320-N are separated by gaps that remain substantially constant at different distances from the conductive layer 310.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc.

In some embodiments, nano-structures can be fabricated by a different process as shown in FIGS. 16A to 16F. A two-layer structure 362 includes a conductive layer 335 and a substrate 330. The conductive layer 335 can be made of titanium (Ti) or nickel (Ni), and can be electrically and thermally conductive. The substrate 330 can be an n-type silicon flat wafer (3-8 Ω-cm) or oxidized (30-50 nm $SiO_2$) p-type silicon flat wafers (5-10 mΩ-cm). The thickness of this conductive metal layer 335 can be controlled in the range of 100 Å-1,000 Å. An adhesion layer (e.g. made of Ag) can be deposited to the metal layer 335. The thickness of the conductive layer 335 can be optimized for applying an electric bias to the sensing surface for trace chemical detection and further for applying a lower temperature to the sensing surface to enhance sensitivity of trace chemical detection.

Figure 16A:
FIGS. 16A-16D, 16G, and 16H are cross-sectional views of the nano-structure formed on the multi-layer layer structure after the fabrication process.
Figure 16D:
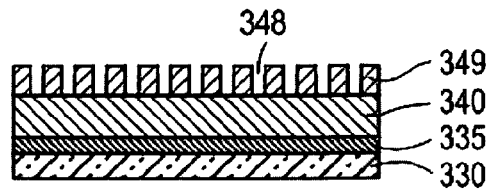
Figure 16B:
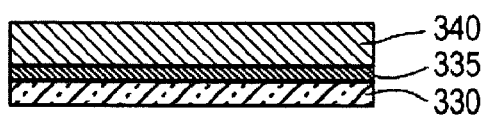

In FIG. 16B, a noble metal layer 340 is deposited on top of the conductive layer 335. The noble metal may be a silver layer, e.g., Ag layer having a thickness of 10-200 nm. In FIG. 16C, a second metal layer 345 is deposited on top of the noble metal layer 340. The second metal layer 345 can include aluminum with a purity level of approximately 99.999% and a thickness in the range of 1.0-10.0 µm. The aluminum layer 345 is then annealed at 400° C.-500° C. in a $N_2$ purged furnace for 2-5 hours to recrystallize the Al film.

In FIG. 16D, an anodization process is carried out to produce a porous structure in a form of porous aluminum oxide 345'. A top view is shown in FIG. 16E where the porous structure is formed with naturally self-assembled hexagon-shaped nano pore-array that includes a plurality of pores 348 surrounded by hexagon-shaped pore wall 349. Neighboring pores 348 have a center-to-center distance D. After removing top anodized layer and the barrier layer by a wet chemical process, a second anodization process is carried out to consume all Al metal so that the barrier layer and top porous $Al_2O_3$ layer 345' are right above the noble metal layer 340.

Then a wet etch process is performed to widen the pores 348 and to remove the barrier layer at the bottom of the pores 348. As the wet etch process proceeds, as shown in FIG. 16F, the pores 348 are widened and the walls 349 surrounding the pore become thinner. The etch process can be controlled to form a plurality of nano-holes 348 surrounded by wall 349. Alternatively, the etching of the pores 348 can widen the pores 348 so much such they touch each other, which can produce a hexagonal array of quasi-triangle nano columns 349'.

Figure 16G:
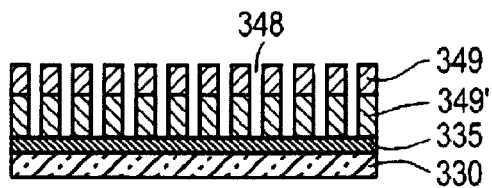
Figure 16C:
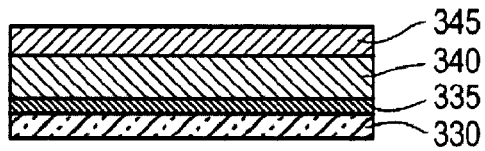
Figure 16H:
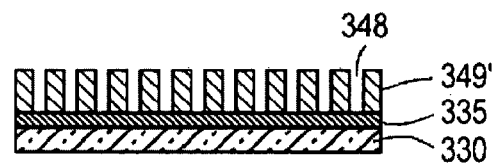
Figure 16F:
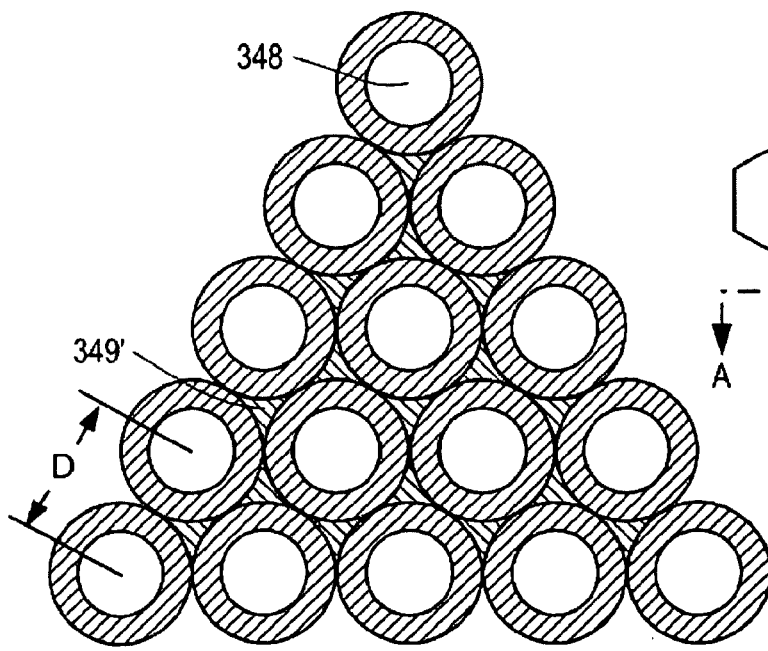
FIGS. 16E and 16F are top views of the nano-structure formed on the multi-layer layer structure after the fabrication process.
Figure 16E:
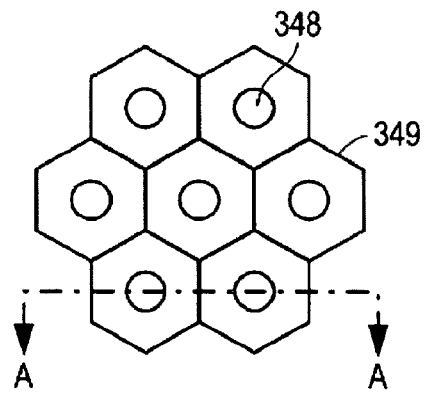

In FIG. 16G, the noble metal layer 340 is etched down and the pores 348 are extended downward to reach the conductive titanium layer 335. In FIG. 16H, a wet oxide etch is performed to remove the aluminum oxide followed by a wet metal etch to remove the aluminum residue at the bottom of the pores 348. The aluminum oxide 315 and the residue aluminum film 315 at the bottom of the porous aluminum layer 315 are removed to form an array of nano rods 349' having controlled heights, diameters and well-defined inter-rod distances. The array can have quasi-triangle periodic cells.

The nano rods are substantially straight and are substantially perpendicular to the substrate 330 and the conductive layer 335. The nano rods can have substantially the same or similar widths. Neighboring nano rods are separated by gaps that remain substantially constant at different distances from the conductive layer 335.

In some embodiments, a chemical sensor compatible with FIGS. 1A and 1C can be prepared by introducing nano particles as described above on a substantially structured or unstructured (i.e. flat) substrate, or a sample solution. The trace chemical or biological substance can first be mixed with the nano particles in a solution to allow molecules of the trace chemical or biological substance to be adsorbed onto the nano particles. The sample solution containing the nano particles are then introduced onto the structured or unstructured surface of the chemical sensor. In other words, nano surface structures can be prepared by coating the surface of the sensor 105 by a solution containing a colloidal suspension of nano particles. The nano particles can be formed by a metallic materials (such as Al, Ag, Au, Cu, Fe, Co, Ni, Cr, Zn, Sn, Pd, Pt, and their alloys), oxide material (such as titanium oxide, silicon oxide, zinc oxide, etc), or a polymeric material. Oxide or polymeric particles can be doped with metal ions or coated with a conductive material. The colloidal suspension can include single nano particles or clusters of nano particles. A nano surface structure is formed after the solution applied to the sensor surface. The solution can evaporate, leaving the nano particles adsorbed with the target molecules on the sensor surface.

In some embodiments, diseases can be identified by analyzing Raman spectra obtained from body fluids from a patient using the light scattering probe 100 as described above in relation to FIGS. 1A-2, 6B, 7-9B. A body fluid obtained from an individual person can be directly introduced onto a sensor (105 in FIG. 1A) or mixed with a sample solution (720 in FIG. 7) containing nano particles. Light scattering and Raman spectral analyses can be conducted as shown in FIGS. 1A-1C or in FIG. 7. Alternatively, the sample solution containing the nano particles can be introduced on a structured or unstructured surface of a sensor, as described above, which is used in subsequent light scattering and Raman spectral analysis.

Figure 17:
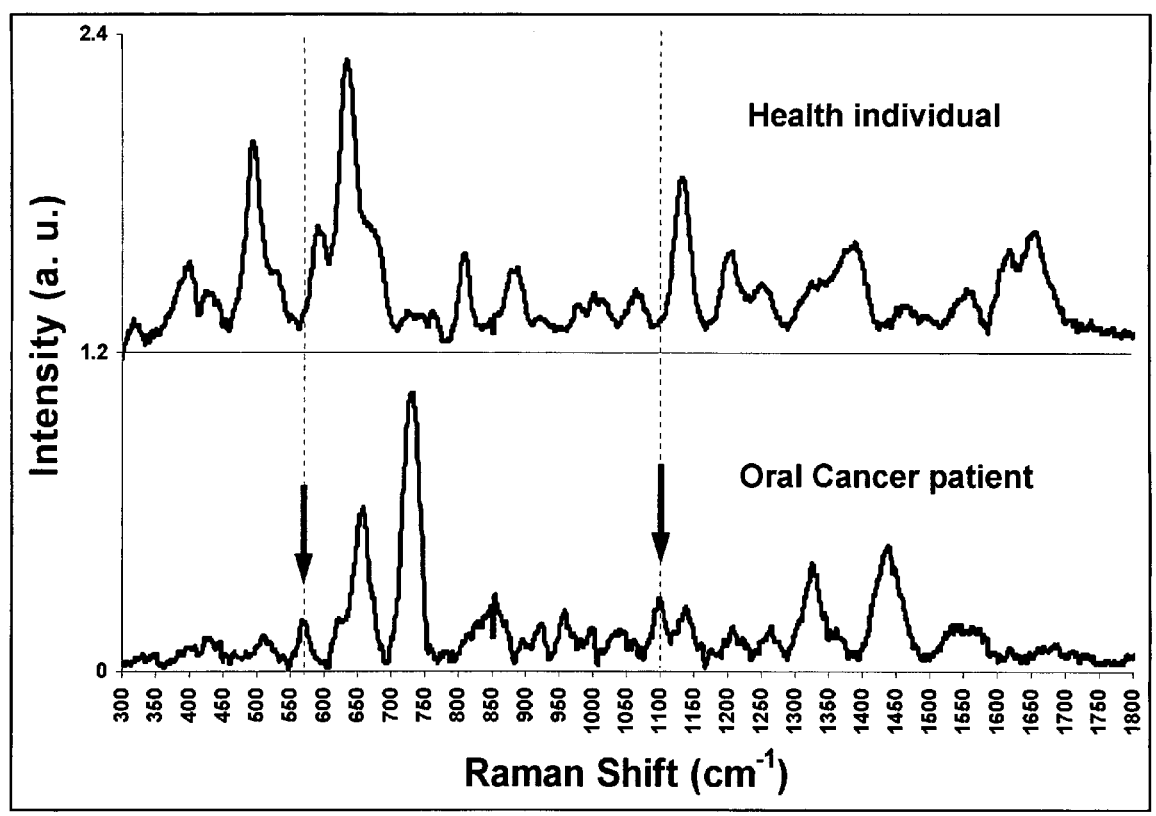
FIG. 17 illustrates an exemplified Raman spectral signature for oral cancer detected in the saliva of an oral cancer patient by the disclosed Raman scattering probe.

Referring to FIG. 17, the Raman spectrum obtained from a saliva sample from an oral cancer patent has show two signature spectral peaks respectively around, for example, 560 $cm^{-1}$ (in the region from 530 $cm^{-1}$ to 570 $cm^{-1}$) and 1100 $cm^{-1}$ (in the region from 1185 $cm^{-1}$ to 1105 $cm^{-1}$) which are absent in a healthy individual without the oral cancer. The signature spectral peaks at 560 $cm^{-1}$ and 1100 $cm^{-1}$ are associated with molecular vibrations for C—S, S—S, and O—P—O ($PO_2$) bonds in, for example, cysteine, ATP, ADP, and other phosphate containing biological samples. The identification of these spectral signatures can include the steps: a spectral band is first selected at Raman peaks with Raman shift in unit of $cm^{-1}$ (wave number) of each spectral signature. A background scattering intensity level is determined. The peak intensity level, relative intensity or integrated area of the peak, is calculated. A signal-to-noise ratio is calculated using the peak intensity and the background level. If the signal-to-noise ratio is higher than a predetermined threshold (e.g., 3 or higher), the spectral signature of a Raman peak is positively identified. The identification of spectral signatures for detecting diseases and drug use can be assigned by statistical analysis and several computation algorithms such as dendrograph classification and Principal Component Analysis. A patient can be diagnosed as likely having oral cancer or at an early stage of an oral cancer if spectral signatures around 560 $cm^{-1}$ and 1100 $cm^{-1}$ are both identified. Appropriate doctors and patients themselves may be alerted for further testing using the same or other types of diagnosis techniques.

Figure 18:
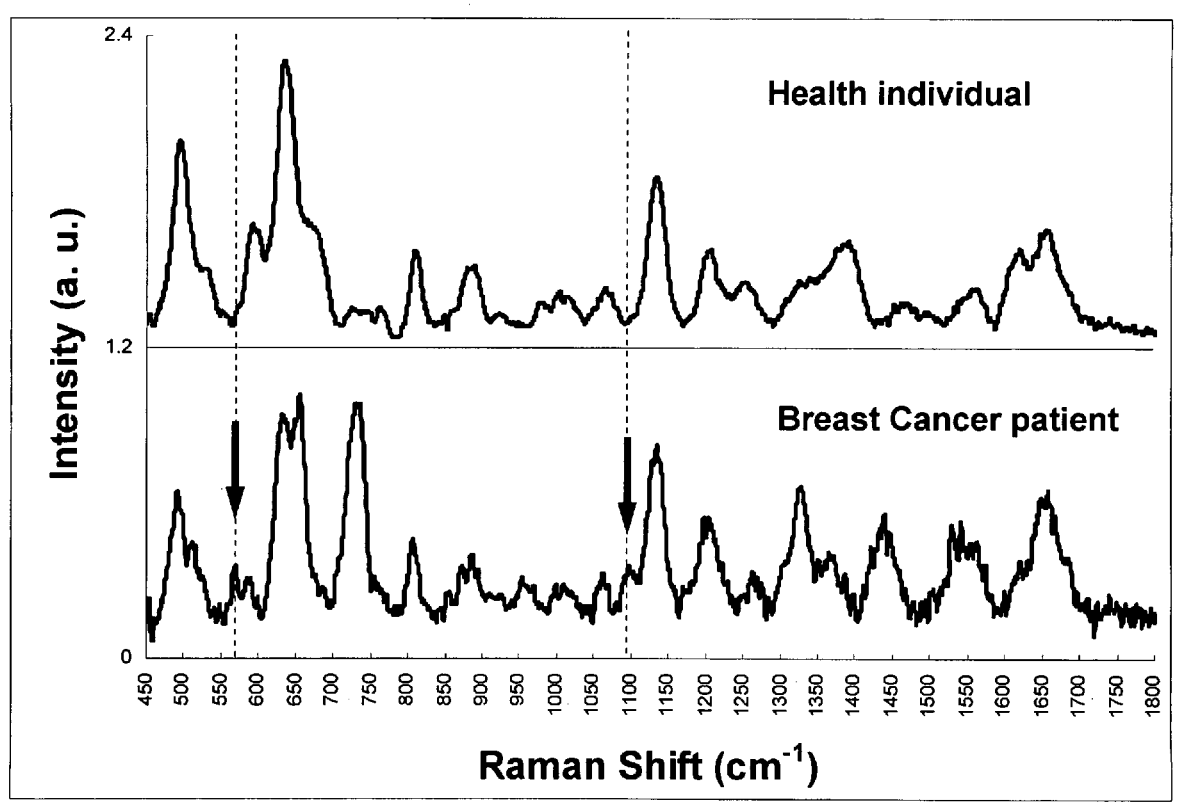
FIG. 18 illustrates an exemplified Raman spectral signature for breast cancer detected in the saliva of a breast cancer patient by the disclosed Raman scattering probe.
Figure 19A:
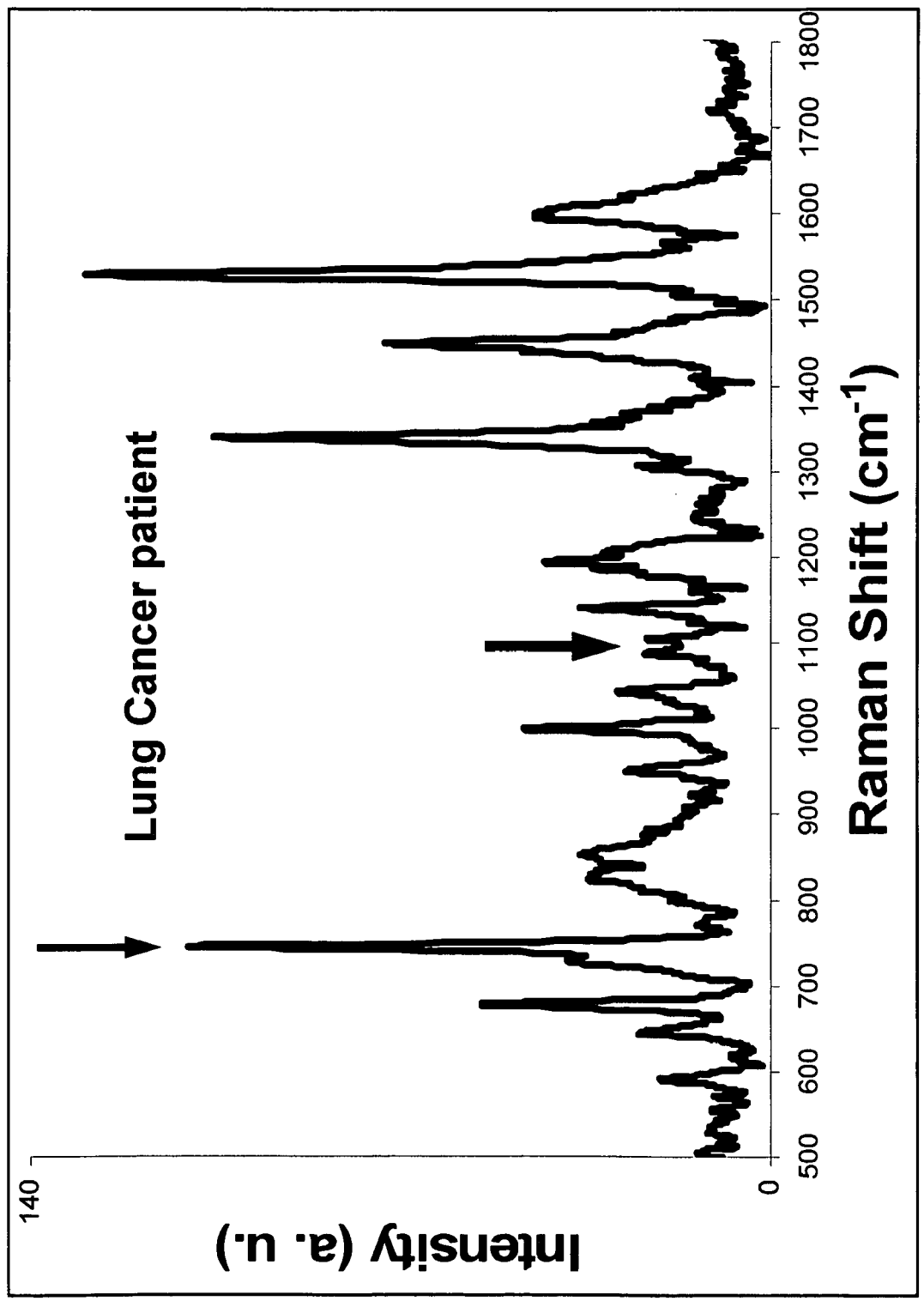
FIGS. 19A and 19B illustrate an exemplified Raman spectral signature for lung cancer detected in both the saliva and the serum of a lung cancer patient using the disclosed Raman scattering probe.
Figure 19B:
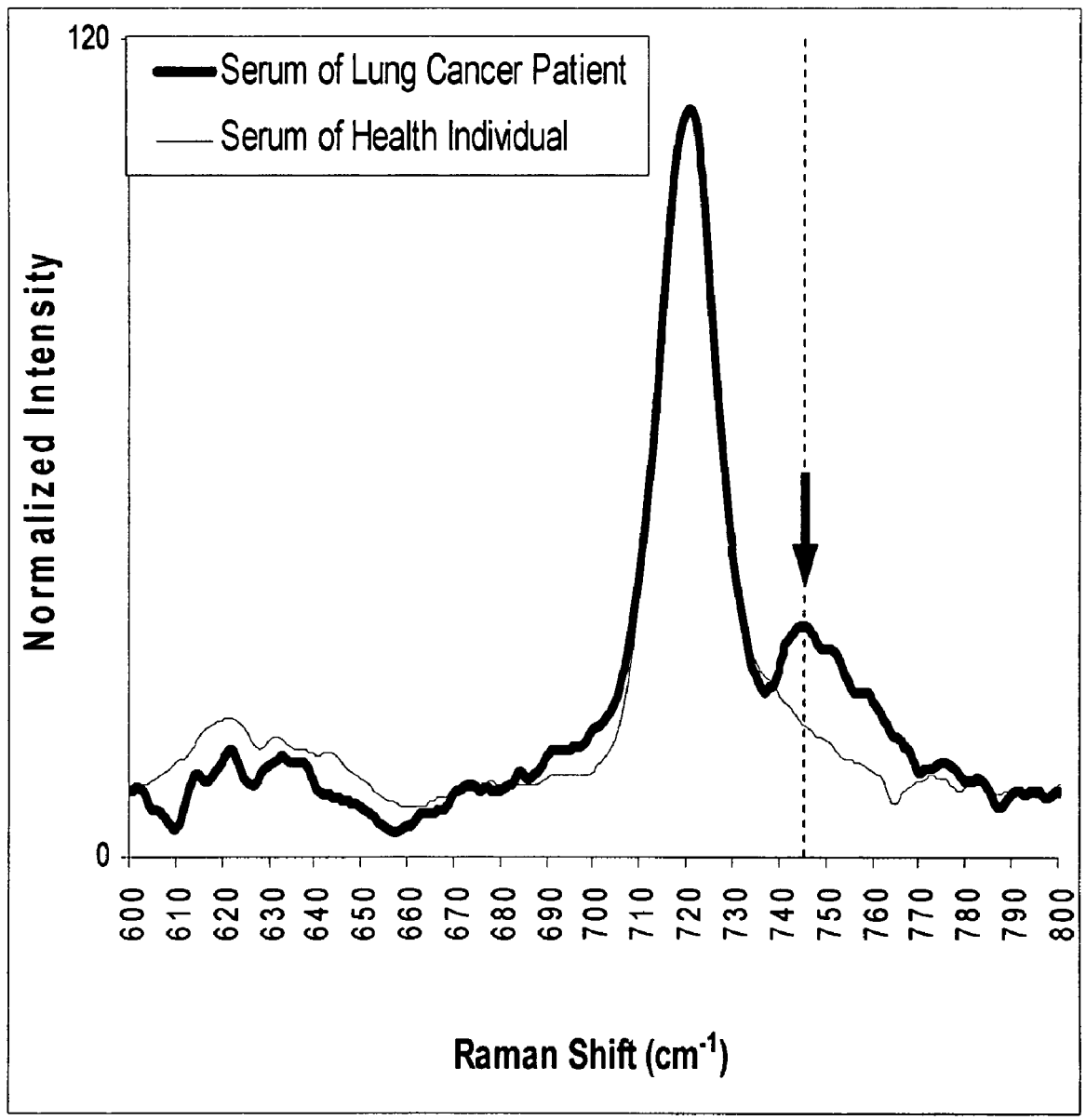
Figure 20:
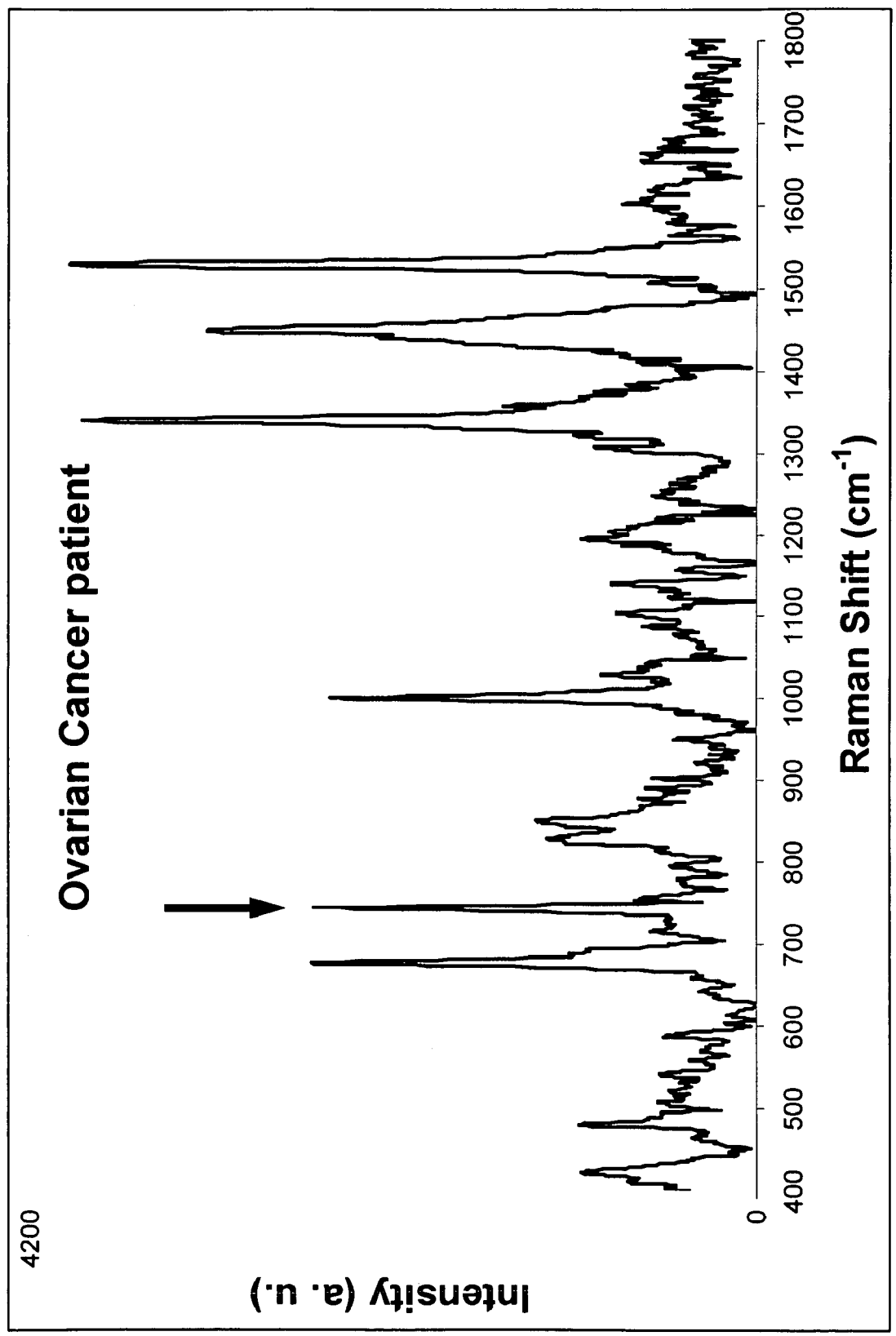
FIG. 20 illustrates an exemplified Raman spectral signature for ovarian cancer detected in the serum of an ovarian cancer patient by the disclosed Raman scattering probe.
Figure 21:
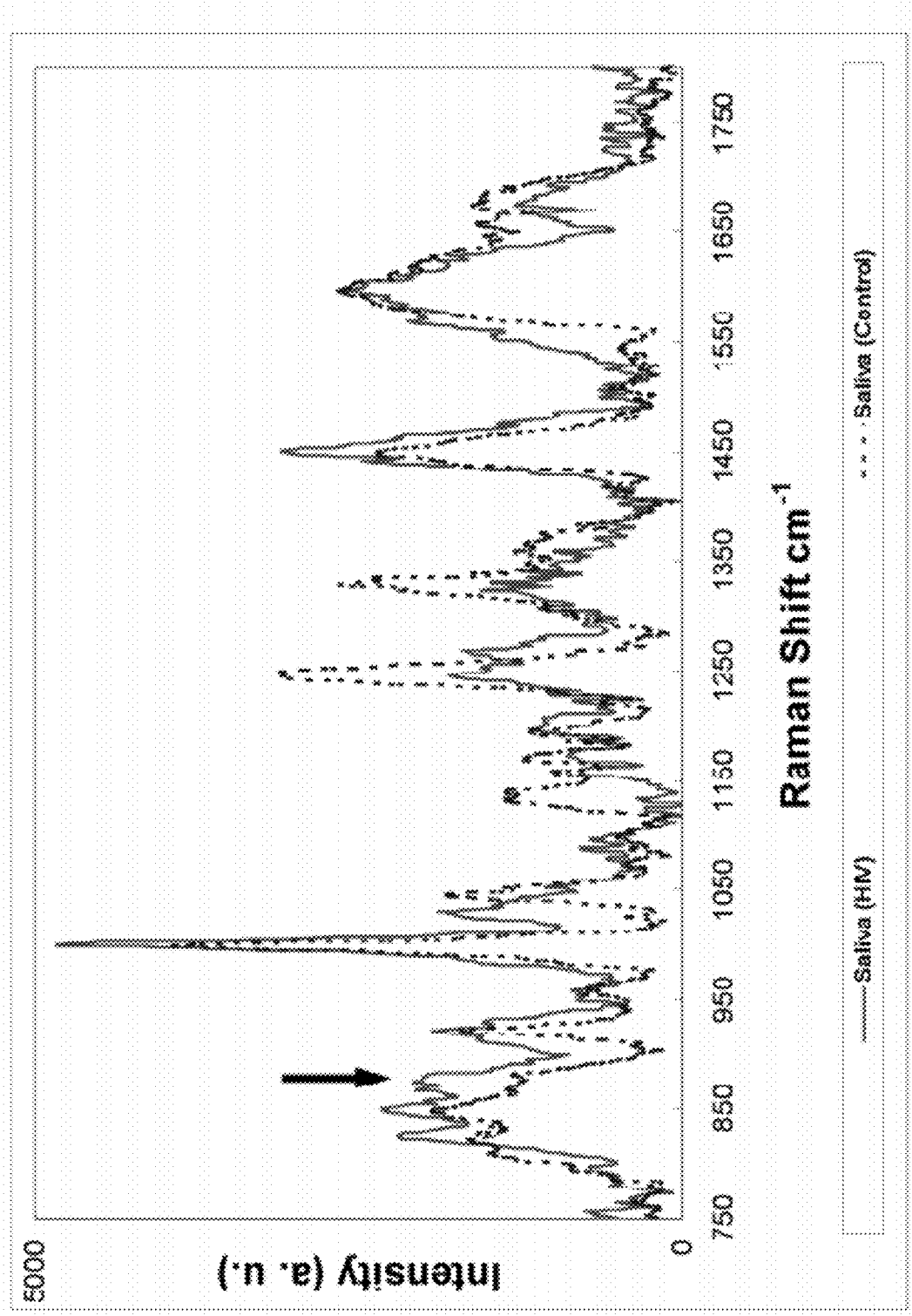
FIG. 21 illustrates an exemplified Raman spectral signature for HIV detected in the saliva of an HIV patient by the disclosed Raman scattering probe.
Figure 22:
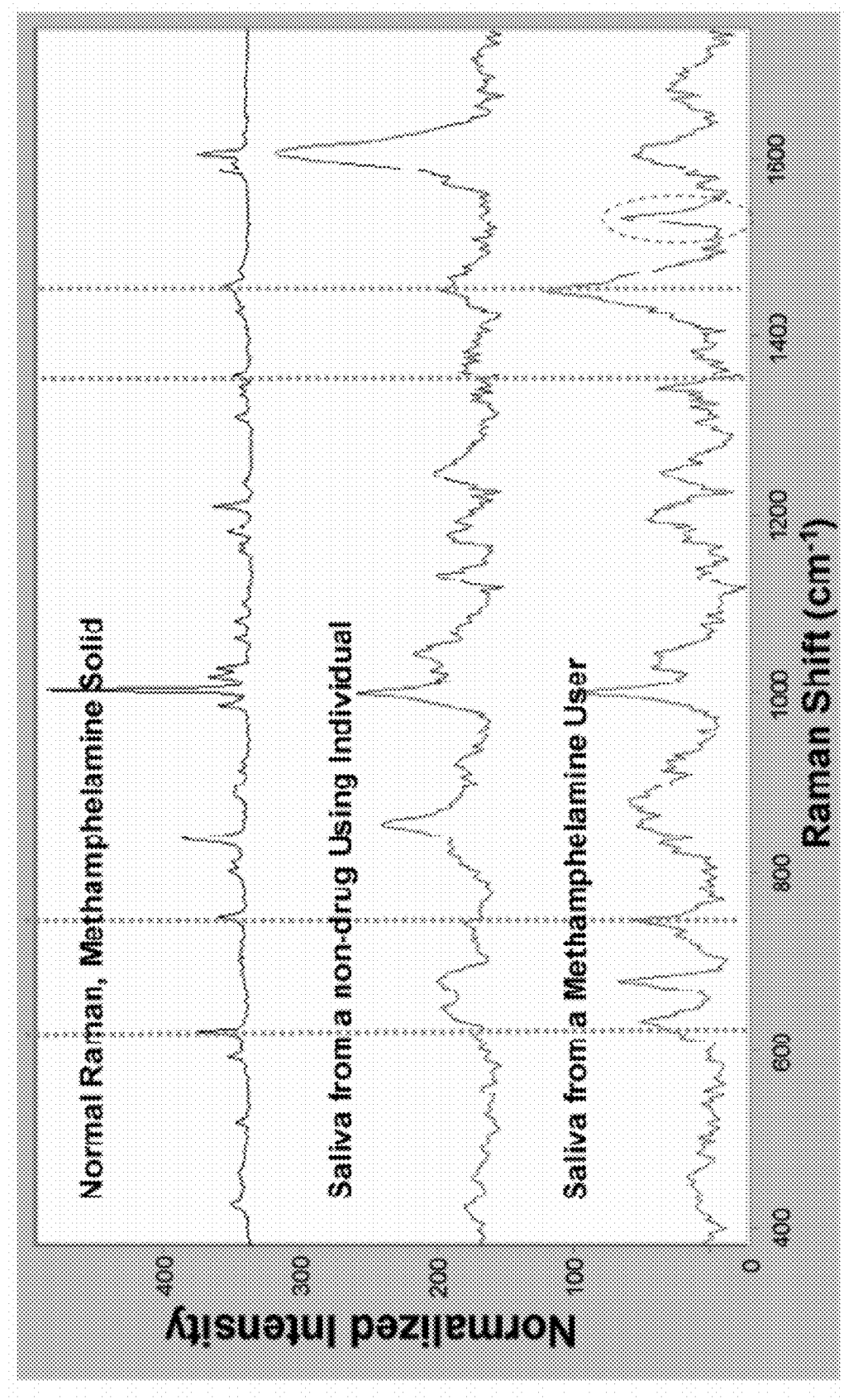
FIG. 22 illustrates an exemplified Raman spectral signature for illicit drug use detected in the saliva of an illicit drug user by the disclosed Raman scattering probe.

The disclosed systems and methods can also be used to estimate glucose level so that to evaluate diabetes status. A signature spectral peak in the region from 1115 $cm^{-1}$ to 1135 $cm^{-1}$, for example, 1124 $cm^{-1}$, which is associated with molecular vibration of glucose, in a Raman spectrum obtained from a saliva sample from a diabetes patient can provide key evidence for diagnosing diabetes. The intensity, relative intensity or integrated area of this Raman peak, can be used to evaluate glucose concentration of a body fluid from a patient to score potential diabetes level. Similarly, referring to FIGS. 18-20, breast cancer can also show spectral signatures in Raman spectrum obtained from saliva around 560 $cm^{-1}$ and 1100 $cm^{-1}$ (FIG. 18). Saliva and serum samples obtained from lung cancer and ovarian cancer patients can have a Raman spectral signature at around 745 $cm^{-1}$ (FIGS. 19 and 20). The signature spectral peak at 745 $cm^{-1}$ is associated with molecular vibrations for C—S bonds in phosphate, or O—P—O vibration in Z-DNA. HIV can have a spectral signature in Raman spectrum obtained from a serum sample in the region of 865 $cm^{-1}$-885 $cm^{-1}$, for example, around 870 $cm^{-1}$ (FIG. 21). The disclosed systems and methods can also be used to identify illicit drug such as heroin, methamphetamine cocaine, caffeine, morphine, codeine, amphetamine, ephedrine, papaverine, narcotine, MDMA, etc. FIG. 22 shows Raman spectra from a methamphetamine solid (a type of illicit drug), a saliva sample of a non-drug using individual, and a methamphetamine drug user. The Raman spectrum from a drug-user's saliva sample shows a characteristic peak at around 1030 $cm^{-1}$ and 1535 $cm^{-1}$, which can be used to indicate illicit drug use. The disclosed methods and systems can also be used to detect doping (e.g., hormone) in athletes during international sports competitions such as the Olympic Games.

Figure 23:
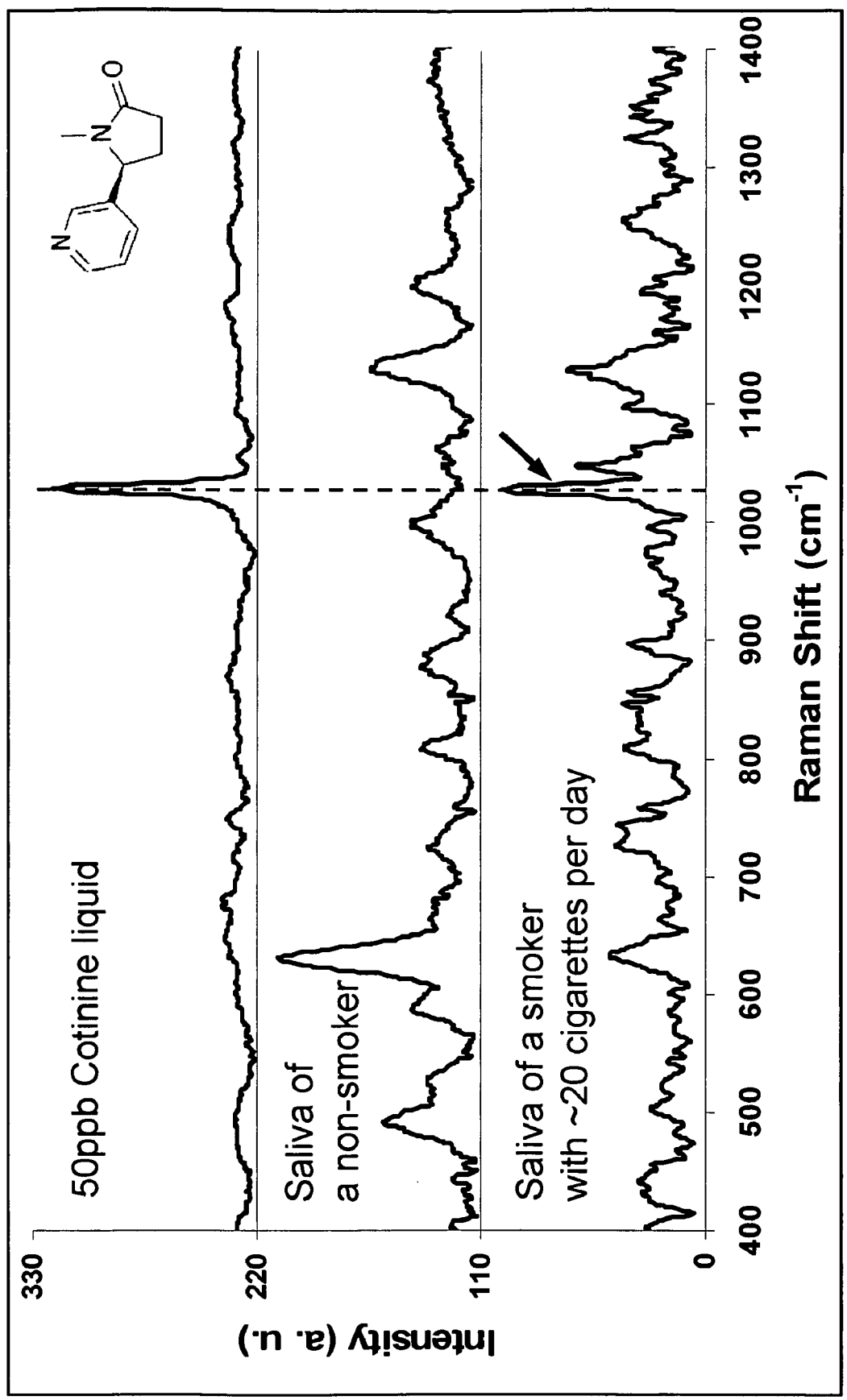
FIG. 23 illustrates an exemplified Raman spectral signature for the smoking status detected in the saliva of a smoker by the disclosed Raman scattering probe, with a comparison of a Raman spectral signature of the cotinine which is the metabolite of nicotine.

Similarly, referring to FIG. 23, smoking status or secondary smoking status can also show spectral signature at around 1029 $cm^{-1}$ in a Raman spectrum obtained from a saliva sample of a smoker, which is absent in a non-smoking healthy individual. The signature spectral peaks around 1029 $cm^{-1}$ is associated with molecular vibration mode of cotinine which is metabolite of nicotine.

Figure 24:
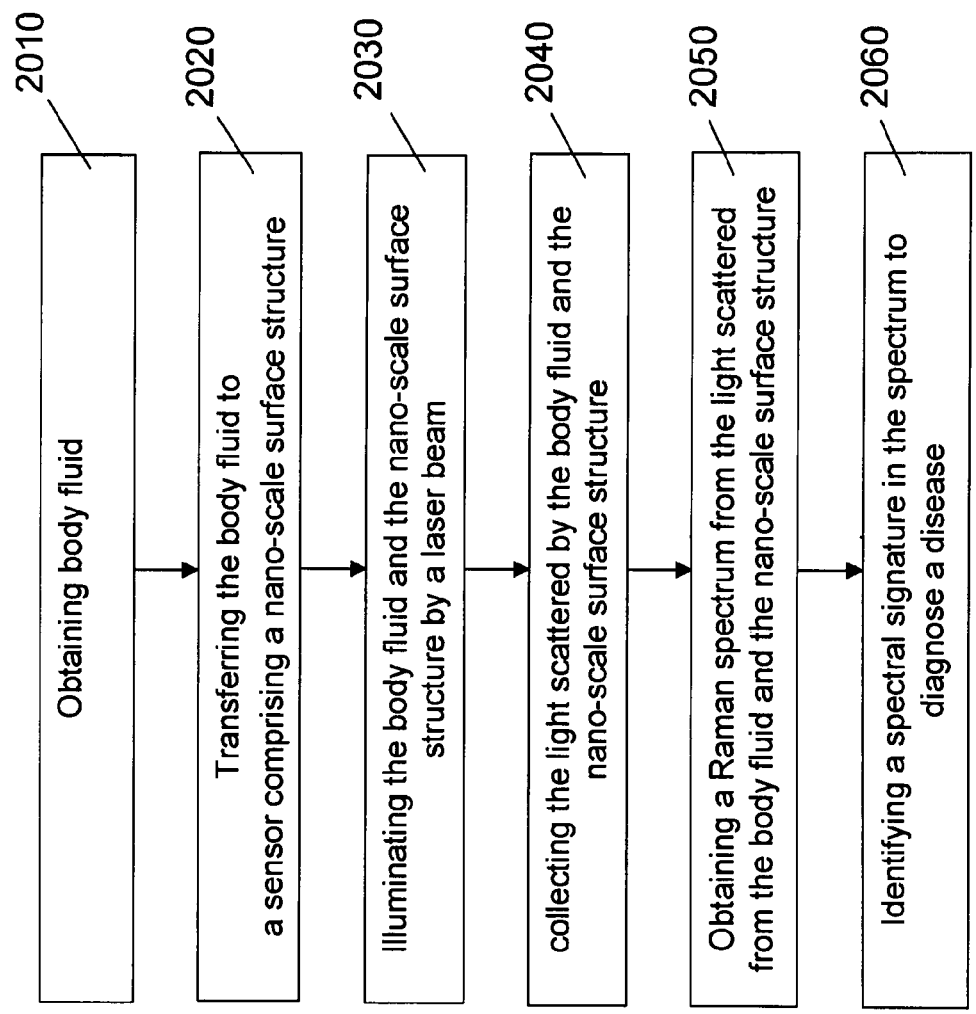
FIG. 24 is a flowchart for non-invasive disease diagnosis using the disclosed Raman scattering probe.

The non-invasive disease detection and diagnosis using the disclosed Raman scattering probe can include one of more of the following steps: referring to FIG. 24, a body fluid is first obtained from a patient or an illicit drug user (step 2010). Due to the high sensitivity of the disclosed Raman scattering sensors, the amount body fluid can be rather small. For example, the volume of the body fluid obtained from the patient can be in a range from about 100 pl to 4 ml. Examples of the body fluid can include blood, saliva, urine, serum, tear, sweat, and stomach fluid. After centrifuge, the body fluid is next transferred to a sensor (e.g., a RamanNanoChip™) comprising a nano-scale surface structure (step 2020). Molecules in the body fluid are adsorbed to the nano-scale surface structure. A laser beam is applied to illuminate the body fluid, the nano-scale surface structure, and the molecules adsorbed onto the nano-scale surface structure (step 2030). Light scattered by the body fluid, the nano-scale surface structure, and the adsorbed molecules is collected (step 2040).

A Raman spectrum is obtained from the scattered light (step 2050). One or more spectral signatures are identified in the spectrum to diagnose a disease (step 2060). Examples of the diseases that can be detected include lung cancer, breast cancer, stomach cancer, esophageal cancer, thyroid cancer, larynx cancer, liver cirrhosis, a failing kidney, ulcer cancer, ovarian cancer, uterus cancer, cervix cancer, oral cancer, leukemia, colon cancer, bladder cancer, prostate cancer, bronchus cancer, HIV, and drug addiction. As previously described, the one or more spectral signatures are at predetermined wavelengths in the Raman spectrum. The wavelengths and the characteristics of the spectral signatures are specific to the disease to be detected. For example, spectral signatures for oral and breast cancers in a saliva sample can be at around 560 $cm^{-1}$ or 1100 $cm^{-1}$. A spectral signature for lung cancer in a serum sample can be at around 745 $cm^{-1}$ in the Raman spectrum. A spectral signature can include a spectral peak. The spectral signature can be identified when the spectral peak is above certain threshold. For example, a signal-to-noise ratio of the spectral peak relative to the noise background can be above 3 for the spectral signature to be positively identified.

It should be noted that the steps illustrated in FIG. 24 is compatible with and can incorporate one or more steps shown in FIG. 8, which involves using a sample solution containing nano particles.

In some embodiments, the disclosed light scattering probe and disclosed chemical detection methods can be applied in food safety applications, which can include screening illegal additives and verifying useful ingredients in food products. An example for food products is dairy products. Dairy products can include milk, milk powders (e.g., baby formula), cheese, cheese-containing cakes, yogurts, ice creams, milk containing candies, milk containing cookies, milk contained food products, and protein contained food products. A recent serious issue in food safety is related to illegal melamine additive in dairy products such as baby formula, ice cream, and biscuit, etc. The disclosed methods and systems are also applicable to detecting existence and levels of methanol, in alcohol products such as wines, nitrite, sodium cyclamate (sodium cyclohexylsulfamate) and other food additives in food, beverage, alcohol products such as red wine, and wine.

As described above in relation to FIGS. 1A-2, 6A, 6C, and 7-9B, a food sample can be prepared in a solution, which is then introduced on a sensor (105 in FIG. 1A) or mixed with a sample solution (720 in FIG. 7) containing nano particles. Light scattering and Raman spectral analyses can be conducted as shown in FIGS. 1A-1C or in FIG. 7. Alternatively, the sample solution containing the nano particles can be introduced on an structured or unstructured surface of a sensor, as described above, which is used in subsequent light scattering and Raman spectral analysis.

As described above in relation to FIGS. 1A-2, 6A, 6C, and 7-9B, chemical or biological sample can be prepared in a solution, which is then introduced on a sensor (105 in FIG. 1A) or mixed with a sample solution (720 in FIG. 7) containing nano particles or carbon nano tubes. One way to prepare sample solution is to directly mix chemical and biological substance contained sample, such as liquid, solid, powder, sol gel, aerosol, etc., into test sample solution containing nano particles; the other way to prepare sample solution is to mix gas phase chemical or biological substance into the test solution using the sample tube with number of tiny holes at the end of tube emerging into a solvent solution, which gas phase sample is continuously purged into the solvent solution, then prepare the sample solution by mix the solvent solution with the solution containing nano particles. The gas purging time is in the range from 1 min to 2 hours, the gas purging pressure is in the range from 1 atm to 5 atm. the dimension of number of holes at the end the gas sampling tube is from 5 μm to 50 mm, the dimension of inner diameter of the gas sampling tube is from 20 μm to 500 mm. The chemicals containing in the gas or aerosol phase sample include ammonia, benzene, toluene, m-xylene, o-xylene, p- xylene, sulfur dioxide, nitrogen monoxide, nitrogen dioxide, neovaricaine, dimethyl formamide, etc. Light scattering and Raman spectral analyses can be conducted as shown in FIGS. 1A-1C if the sample solution is placed onto the surface of a sensor, or in FIG. 7. Alternatively, the sample solution containing the nano particles can be introduced on an structured or unstructured surface of a sensor, as described above, which is used in subsequent light scattering and Raman spectral analysis.

In some embodiments, milk sample solutions are prepared from a milk solution by respectively applying with melamine additive at concentrations of 1 ppm (parts per million), 2 ppm, 5 ppm, and 50 ppm. The milk sample solutions are separately applied to a sensor (105 in FIGS. 1) or introduced into a sample solution (720 in FIG. 7) containing nano particles. The melamine additive includes melamine and melamine cyanurate. Raman spectra are obtained using the light scattering probe and method described above. A typical volume for the food sample solution is in a range from about 100 pl to 1 ml.

Figure 25A:
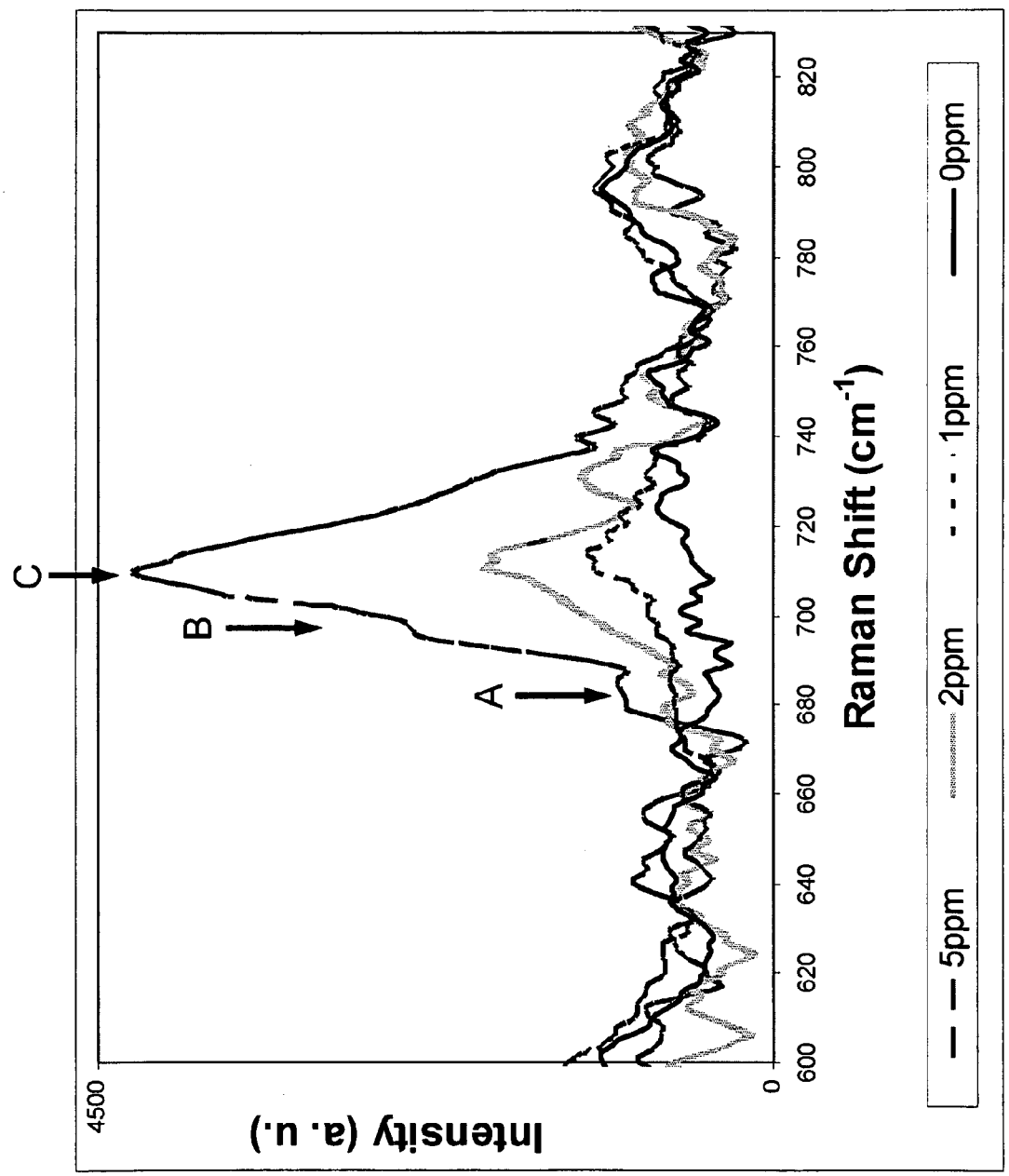
FIGS. 25A and 25B illustrate Raman spectra having spectral signatures for an illegal and harmful chemical (melamine) detected at different concentration levels in a milk product.
Figure 25B:
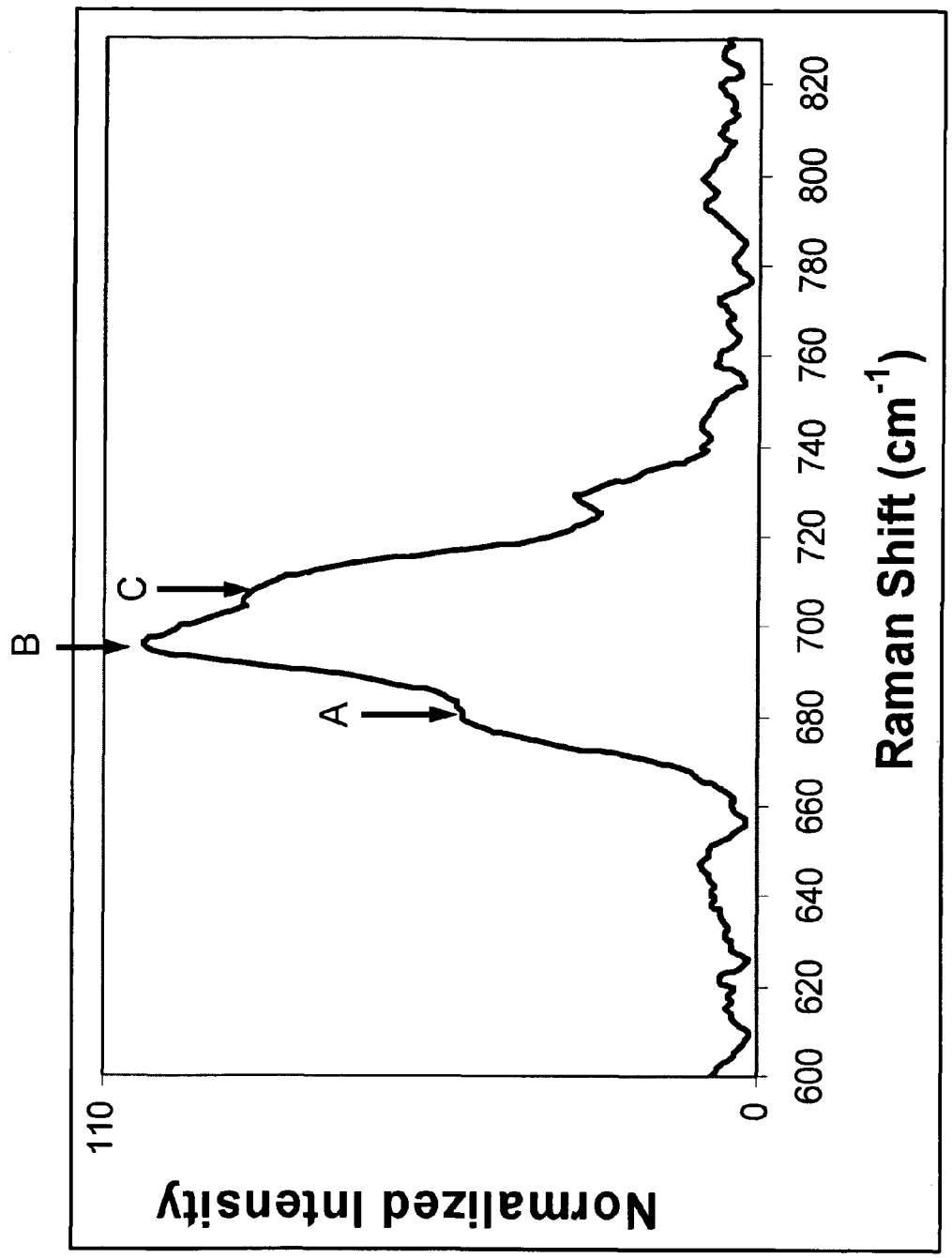

Raman spectra having spectral signatures for an illegal and harmful chemical (melamine) detected at different concentration levels in a milk product. FIG. 25A illustrates Raman spectra obtained from the milk sample solutions with melamine additive respectively at 0 ppm (no melamine additive), 1 ppm, 2 ppm, and 5 ppm concentration levels. FIG. 25B illustrates a Raman spectrum obtained from the milk sample solution having melamine additive at 50 ppm level. The Raman spectra shown in FIGS. 25A and 25B comprise Raman signature bands around 700 $cm^{-1}$, which are approximately at around 678 $cm^{-1}$ (Band A), 698 $cm^{-1}$ (Band B), and 712 $cm^{-1}$ (Band C), respectively. These observed Raman peaks are assigned to be vibration of the ring breathing II mode and involves in-plane deformation of the triazine ring of melamine molecule, or a ring out of-plane bending vibration of melamine cyanurate molecule. Moreover, it was observed that Band A at around 678 $cm^{-1}$ increases in relative strength among the three bands as the melamine concentration is increased. In contrast, Band C at about 712 $cm^{-1}$ decreases in relative strength as melamine concentration increases. These two trends can be clearly seen by comparing the Raman spectra at the 5 ppm (FIG. 25A) and 50 ppm (FIG. 25B) melamine levels. Note that melamine cyanurate (needle-shaped micro-sized white precipitates) is formed when melamine and cyan uric acid exist in the solution together under certain condition.

Figure 26:
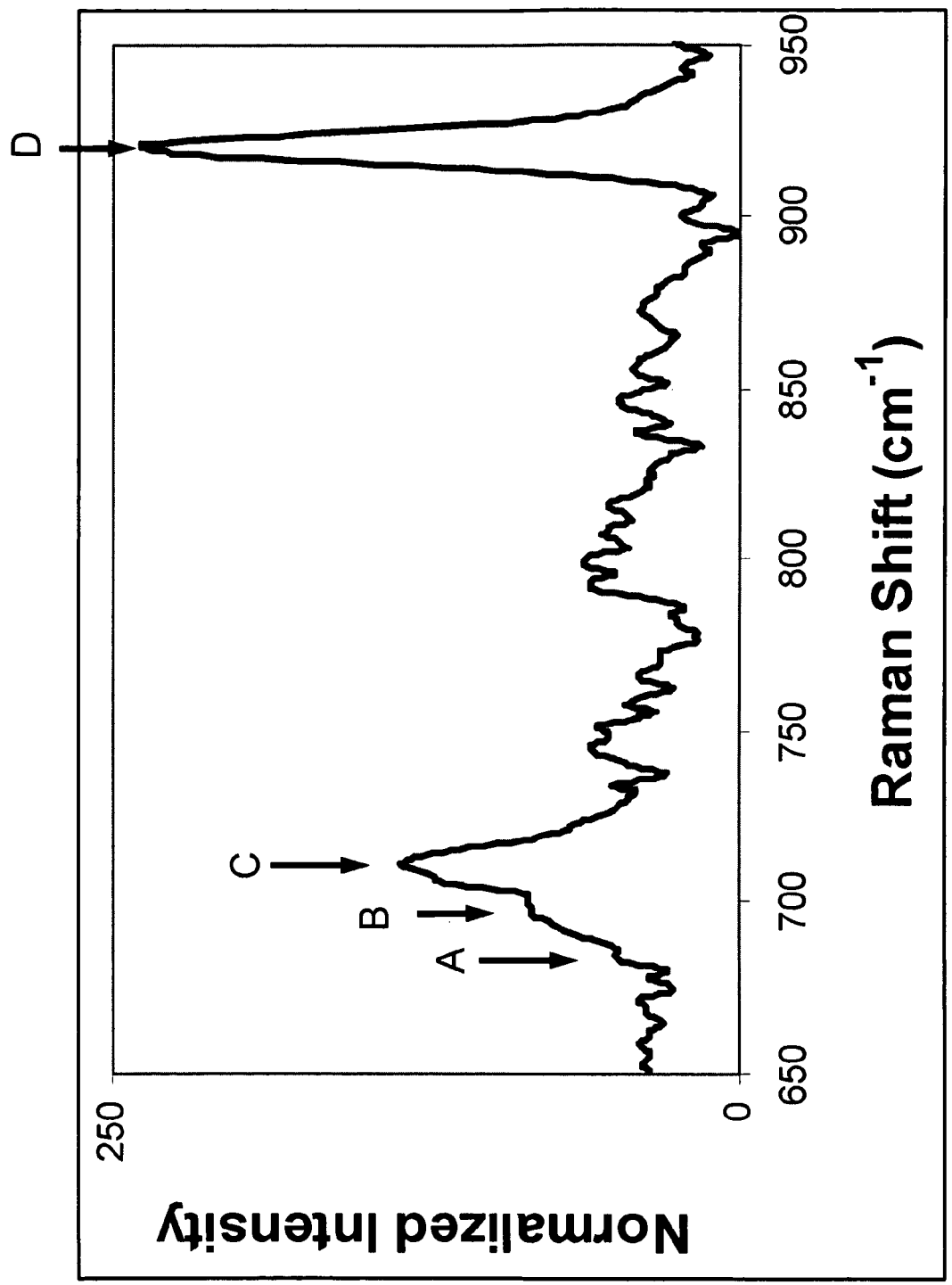
FIG. 26 illustrates a Raman spectrum having a spectral signature for melamine detected in a milk solution using 918 $cm^{-1}$ Raman band of the acetonirile as an internal standard reference.

In another example, acetonitrile solvent can be added to a sample milk solution as an internal standard reference for the Raman scattering measurement. Acetonitrile is used as a solvent because it was found that the Raman scattering strength is not or weakly coupled to test solution. Referring to FIG. 26, a Raman spectrum is obtained, with the Raman spectral signature around 700 cm$^{-1}$ (Band A, B and C), from a milk solution having a melamine concentration at 5 ppm and with the addition of the acetonitrile using the above described system and methods. A Raman band (Band "D") is found at around 918 cm$^{-1}$-921 cm$^{-1}$, which can be used as an internal standard reference for calibrating Raman band frequency and intensity. Another Raman band exists at around 1640 cm$^{-1}$.

Figure 27:
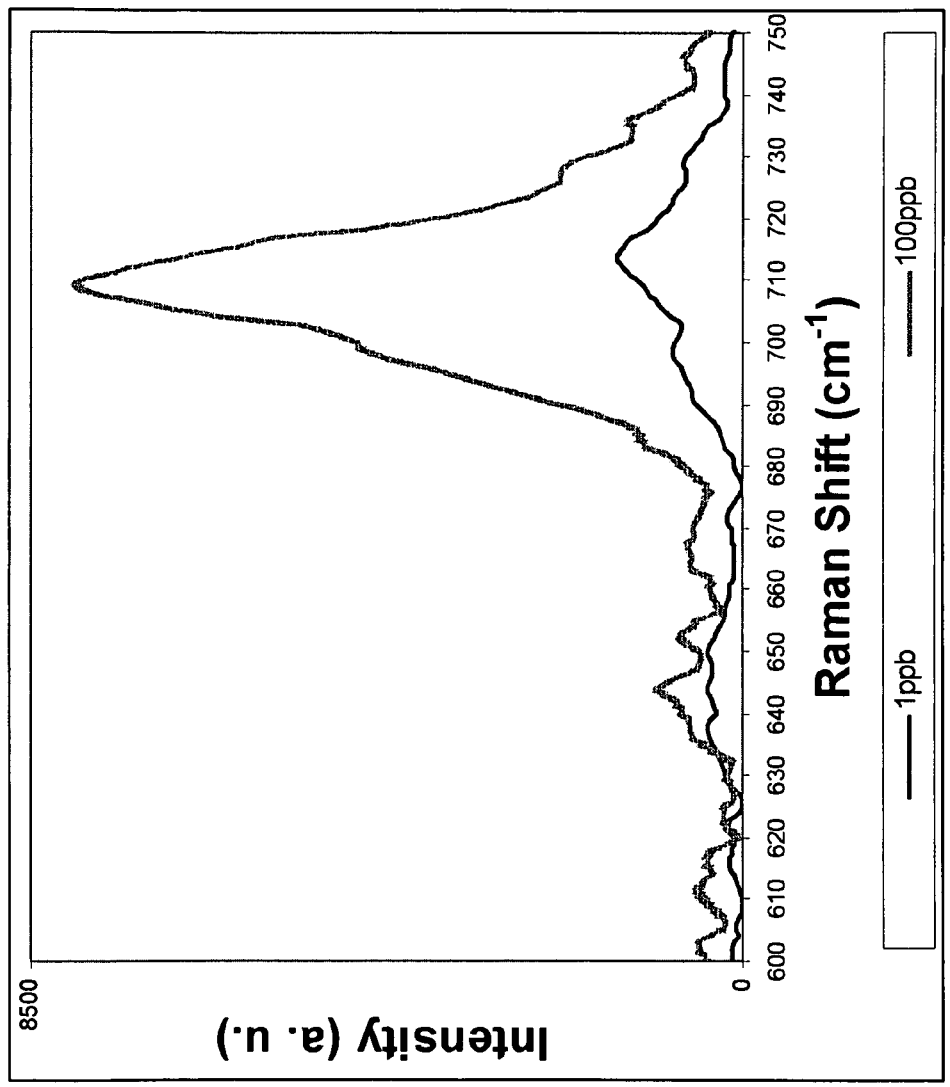
FIG. 27 illustrates Raman spectra having spectral signatures for an illegal and harmful chemical (melamine) detected at different concentration levels in water.

In another example, Raman spectra having spectral signatures for an illegal and harmful chemical (melamine) detected at different concentration levels, 1 ppb (parts per billion) and 100 ppb, in aqueous solution (FIG. 27).

In some embodiments, referring to FIGS. 1B, FIGS. 16F, 16E, and 16H, a metal film is coated on the nano rods 108 (or holes) on the nano surfaces of the sensor 105. The metallic film is electrically connected to an electrode. The metallic film can be formed by a noble metal such as gold. To apply a sample solution to the sensor surface, the sensor is submerged in the sample solution. An electric bias potential is applied to the electrode and the metallic film. The electrical bias potential can be controlled in the range from −3.0 to +3.0V, which can enhance the adsorption of the sample molecules (e.g., melamine molecules) to the nano surfaces, to enhance local electromagnetic filed, and enhance charge transfer between sample molecules and nano surface structures, which can enhance the intensity of Raman scattering from the sample molecules adsorbed on the nano surfaces. The incident laser beam can be projected on the sensor and the scattered light detected while the potential bias is being applied to the sample solution. The Raman light scattering measurement can also be conducted after the electrical bias potential is withdrawn.

In some embodiments, ion-exchange column is a means of separation of interferences from the samples. After sample passed the column, interferences retain on the column and analytes are flute out. The column, for example, $C_{18}$ column, also can be employed that can separate chemicals in different retention times that chemical properties are similar. The final purified sample would result in increasing the limit of detection up to 2-6 orders.

In some embodiments, the detection of chemicals in food or for disease diagnosis can be conducted using an integrated device that is capable of chemical separation and light scattering detection of trace chemicals, biological materials, etc. Details about such an integrated device are disclosed in commonly assigned U.S. patent application Ser. No. 11/761,453, entitled "Integrated Chemical Separation Light Scattering Device", filed Jun. 12, 2007, the disclosure is incorporated by reference herein.

Figure 28:
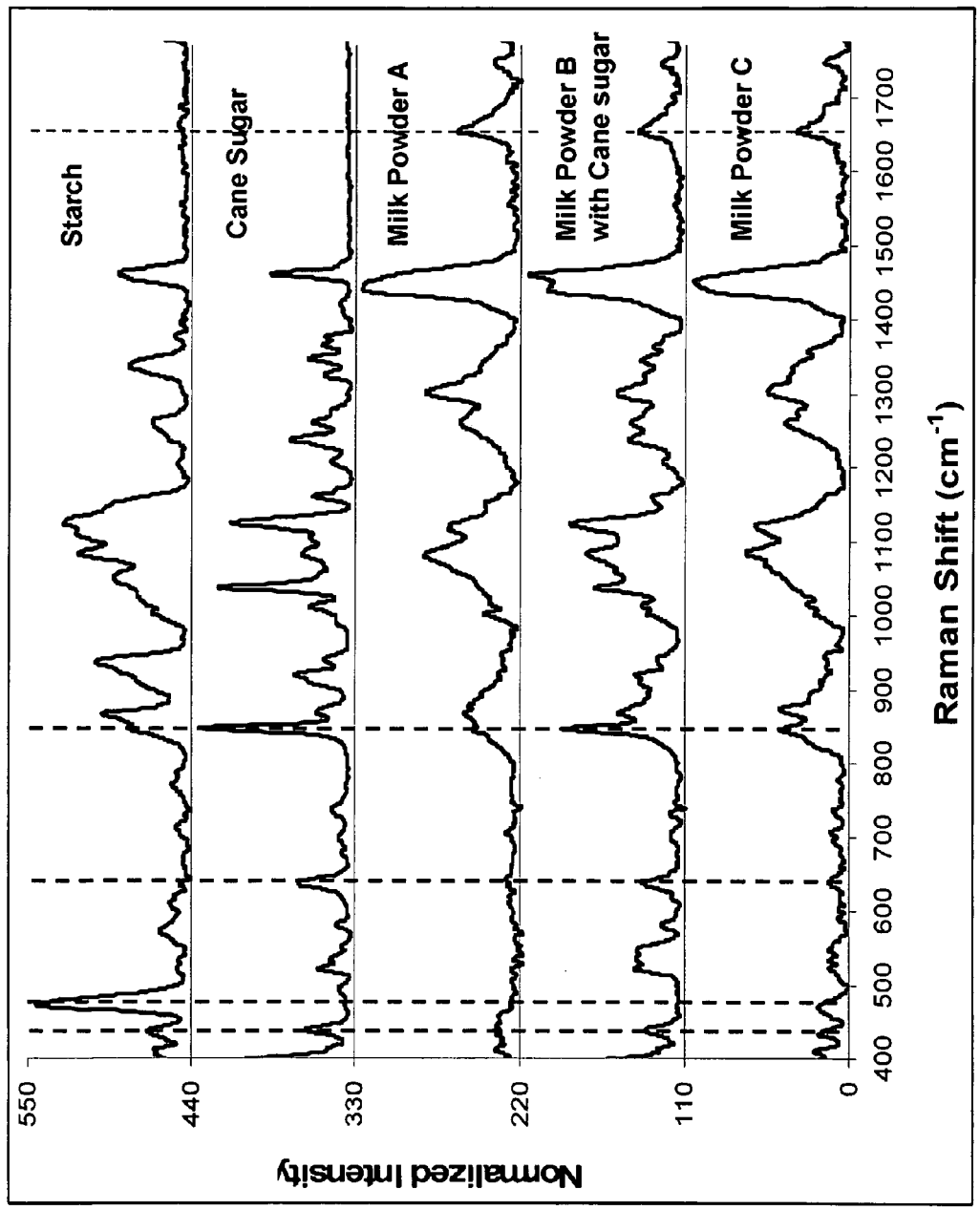
FIG. 28 illustrates Raman spectra for identifying unauthorized additive chemicals in a milk powder product.

In some embodiments, the disclosed light scattering probe and disclosed chemical detection methods can also be applied to detect useful or neutral ingredients as well as illegal or harmful ingredients in food products. FIG. 28 illustrates, from top to bottom, Raman spectra from starch, cane sugar, a milk powder A (a first milk powder brand), a milk powder B (a second milk powder brand) containing with cane sugar additive, and milk powder C (a third milk powder brand). Starch and cane sugars are not supposed to be in normal milk powders. But because starch and cane sugars are white powders, they are not easily detected with normal test methods when they are mixed in milk powder. The Raman spectrum (at the top of FIG. 28) shows a very strong band at around 473 cm$^{-1}$, which provides an evidence for starch content in a milk powder. This signature Raman band can be used to detect if starch is mixed into milk power. The detection method is applicable to the unauthorized mixing of starch containing materials such as flour, rice powder, soybean powder, potato powder, sweet potato powder, etc.

The disclosed systems and methods can also be used to screen the existence of cane sugar in milk powders. The Raman spectra (second from the top in FIG. 28) shows several strong Raman bands (around 850 cm$^{-1}$, 940 cm$^{-1}$, 1020 cm$^{-1}$, 1130 cm$^{-1}$ and so on). The collective characteristics of these Raman bands are visible in the spectrum obtained from milk powder B mixed with cane sugar (fourth from the top in FIG. 28), which is legal since the milk powder B package labeled related cane sugar mixing, but absent from the spectrum obtained from milk powder A without cane sugar additive (third from the top in FIG. 28). On the other hand, the collective characteristics of cane sugar related Raman bands are visible in the spectrum obtained from milk powder C (bottom spectrum of FIG. 28), which the milk powder is illegal sine its package label didn't show related cane sugar. Note that Raman test shows that milk powder C was mixed with both starch and cane sugar without package labeling.

Furthermore, the disclosed methods and systems can be applied to determine level of protein contained in a food product such as in a dairy product. A high concentration of protein in a food product can be reflected by high amide I concentration which carries Raman signature band at around 1658 cm$^{-1}$. The intensity at 1658 cm$^{-1}$ relative to other spectral features can be used to quantify the protein level in a food product such as a milk powder. For example, the three different samples of milk powders in FIG. 28 (shown in the lower three spectra in FIG. 28) are of similar protein levels. The more pronounced peak at 1658 cm$^{-1}$ for milk powder A shows milk powder A contains slightly higher protein level than milk powder B and milk powder C.

The disclosed methods and systems are therefore effective means for detecting protein levels, the existence of cane sugar, starch, and illegal additives such as melamine in milk powders. Moreover, the disclosed systems are compact and portable. The substance detection can be easily conducted on site with a fast turn around time (5 to 10 minutes or even shorter time), which can enable timely and effective authentication and quality verification of milk contained products, such as milk and powder in a wide range of circumstances.

Intensity of Raman signals can be increased by pre-treatment of the test sample. For example, after the test sample is dissolved in a solution, solid particles, unwanted ionic molecules, or undisclosed materials can be removed from the solution by filtering solution using a solid-phase extraction (SPE) column which the major steps include pre-condition by certain solvents, passing sample solution through the column, washing the column by some selected solutions, and obtaining final elute analyte for determination, which is then subject to the light scattering analysis. The removal of solid particles, unwanted molecules, or undisclosed materials can significantly reduced noises in the scattered light from the nano structured surface of a chemical sensor or from a sample solution containing nano particles, so that one is able to carry out quantitative analysis of targeted molecule concentration in know base materials, for example, down to 0.5 ppm concentration of melamine in fresh milk or in product milk, or in milk powder.

When the disclosed methods and systems are applied to food inspection, illegal food additive molecules can be separated from food matrix materials by controlling (e.g. raising) temperature of the sample solution (e.g. 720 in FIG. 7). An illegal food additive is Sudan I which can be separated from capsorubin by controlling temperature in a range of 20° C.-

100° C., more specifically from 40° C. to 80° C., for the period from 1 sec-30 min, or a period from 1 min to 10 min. Other illegal food additives detectable by the disclosed methods and systems include Rhodamine B, Benzoic acid (sometimes found in milk products), hyposulfurous acid, sodium formaldehyde, crysoidine G, boric acid and borax, sodium sulfocyanate, rhodamime B, Lead chrome green, Basic Flavine O, industrial used formaldehyde and NaOH,carbon monoxide, sodium sulfate, industrial surfer, industrial dyes, fructus papaveris, over dosed level of food colorants (e.g. carmine, lemon yellow, allura red AC, sunset yellow, etc.), food preservants, sweeteners (e.g., saccharin sodium salt, Sodium cyclamate), emulsifier (sucrose easter of fatty acid, etc.), swelling agents overdose (KAlSO4, NH4AlSO4, etc.), bleach, sulfer suffumigation, color protectants (nitrate, nitrite, etc.), TiO2, benzoyl peroxide, and KAlSO4. In some embodiments, proteins are separated from mil sample before the detection of melamine using Raman scattering. Proteins can be precipitated or chemically separated from fresh milk or milk powder solution. In one example, the milk solution can be mixed with a high concentration (e.g. super-saturated concentration) of salt such as NaCl to precipitate proteins. In another example, an acetone in acid condition can be added to the milk solution to precipitate proteins. SPE column also be used to remove proteins in the milk solution. The resulting colorless transparent solution is then subject to Raman scattering testing as described above. The removal or precipitation of proteins can significantly reduce random scattering in the Raman spectral signals and thus can significantly increase sign-to-noise ratio in the disclosed techniques, which allows detection melamine at a concentration of 0.2 ppm in fresh milk.

Figure 29:
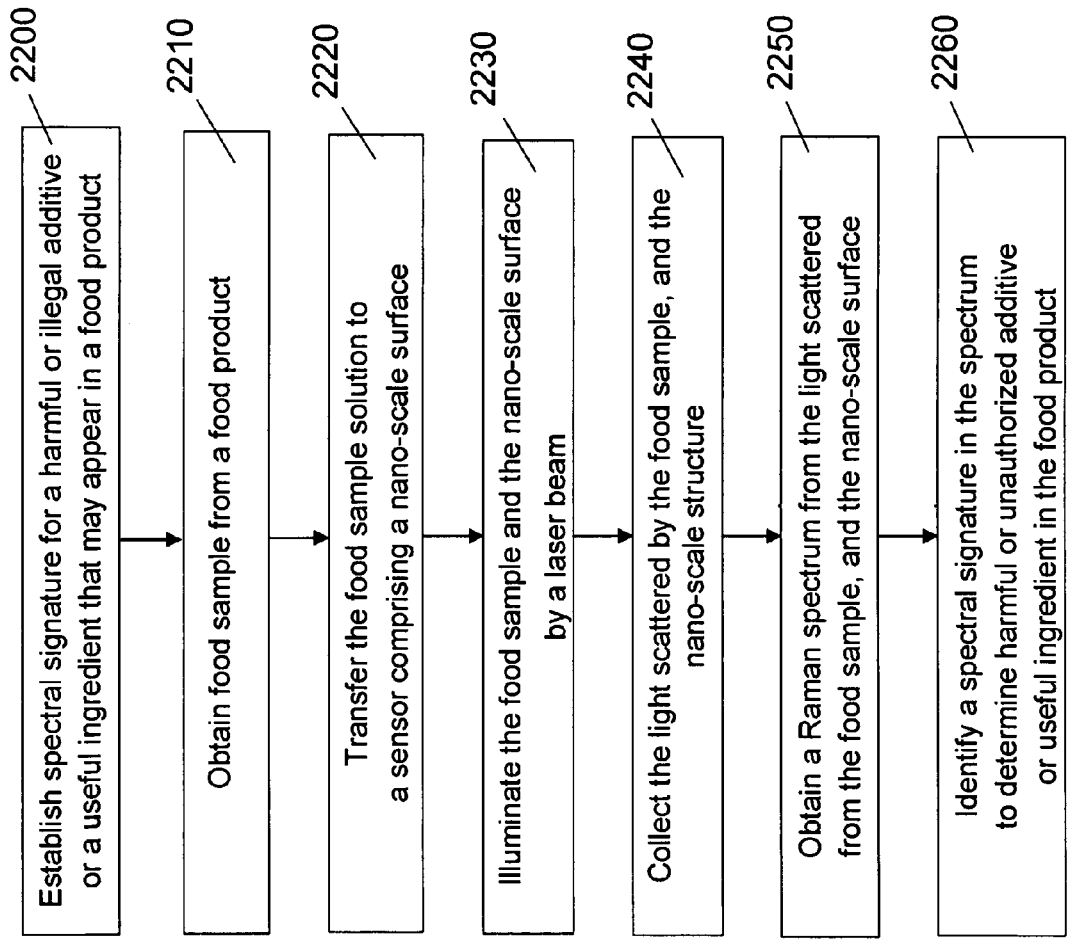
FIG. 29 is a flowchart for detecting harmful chemicals in food products for assuring food safety.

The detection of harmful chemicals in food products using the disclosed Raman scattering probe can include one or more of the following steps: referring to FIG. 29, spectral signatures for harmful or unauthorized, useful ingredients or protein (amide I) that may appear in a food product are first established (step 2200). This can be achieved by conducting Raman scattering measurement on a reference solution of a harmful or useful ingredient applied to nano surface structures on a light scattering sensor as described above. The wavelengths and spectral characteristics (peak height, peak width etc.) can be stored in a library in the spectral analyzer (150 in FIG. 6A). A threshold value can also be determined for the peak height of the spectral signature, which can correspond to certain predetermined concentration of the chemical in the reference solution. In some embodiments, the signal-to-noise ratio of the spectral peak is calculated. The chemical can be positively identified, if the signal-to-noise ratio is above certain threshold (such as 3).

In some embodiments, the sensor used for establishing the spectral signature includes substantially the same nano structures as the sensors to be used for detecting or quantifying chemical substance in the food products. In other words, the dimensions and shape of the nano rods or nano holes, the spacing between the nano rods and nano holes, as well as the material compositions of the nano rods and nano holes are substantially the same for the sensor used for establishing the spectral signature and for in-field testing of food product. For instance, the same sensor model can be used for both purposes. This approach can assure the best matching of spectral characteristics between a measured spectrum and a spectral signature. The approach can also minimize noise that can be caused by structural differences between different sensor structures and material compositions.

In some embodiments, the nano surface structure used for establishing Raman spectral signature for a chemical can be prepared by a test solution that includes the target chemical and a suspension of nano particles. The original sensor surface can be relatively flat. The test solution is applied to the sensor surface. After evaporation, a layer of nano particles adsorbed with the target chemical's molecules are deposited on the sensor surface, which is subject to Raman scattering measurement for establishing the Raman signature. The same procedure can be followed in detection of an ingredient in a food product or a substance in a body fluid from a patient except that the target chemical is replaced by a sample solution of the food sample or the body fluid. To improve test sensitivity and reduce noise in the analysis, the same nano particles and the same solvent are preferably used for the Raman signature testing and the in-field substance detection. In other words, the size distribution and material composition of the nano particles used in establishing the Raman spectral signature and the in-field measurement can be substantially the same.

A food sample is first obtained from a food product (step 2210 in FIG. 29). Due to the high sensitivity of the disclosed Raman scattering sensors, the amount food sample solution can be rather small. For example, the volume of the food sample solution obtained from the field can be in a range from about 100 pl to 1 ml. Examples of the food sample can include dairy products, candies, drinks, alcohol, meat, water products (such as fish, shrimp, etc.), tea, fresh or canned vegetables, fruits, grain products, cereals, corn chips, or potato chips, etc. The food sample can be prepared or dissolved in a solution and transferred to a sensor comprising a nano-scale surface structure (step 2220). Molecules in the food sample solution are adsorbed to the nano-scale surface structure. A laser beam is applied to illuminate the food sample solution, the nano-scale surface structure, and the molecules adsorbed onto the nano-scale surface structure (step 2230). Light scattered by the food sample solution, the nano-scale surface structure, and the adsorbed molecules is collected (step 2240). The test can also be carried out with mixing test sample with test reagent containing noble metal (such as silver Ag, gold Au, etc.) nano particles with averaged particle diameter in the range of about 2 and about 100 nm. Then, light scattered by the mixed sample solution, with or without the nano-scale surface structure, and the adsorbed molecules is collected (step 2240).

A Raman spectrum is obtained from the scattered light (step 2250). One or more spectral signatures are identified in the spectrum to determine harmful or illegal additives and ingredients, or to verify the existence and concentration levels of useful ingredients (step 2260). Examples of the harmful or illegal additives or ingredients, common fertilizer chemicals, weed control chemicals, pesticides, insecticides, antibiotics, hormones, and preserving chemicals, such as melamine, sodium cyclamate (sodium cyclohexylsulfamate) cane sugar, starch, nitrite, nitrate, Sudan I, II, III and IV, malachite green, methomidophos, acephate, DDT, DDV, malathion, fenitrothion, deltamethrin, cypermethrin, methy parathion, phosmet, nitro furan (for example, furanzolidole), dimethoate, chloramphenicol, chlortetracycline, ciprofloxacin, clenbuterol, enorfloxacin, etc. Wavelengths and the characteristics of the relevant spectral signatures in Raman spectra are specific to each chemical to be detected or quantified, as described above in relation to FIGS. 25A-28. A spectral signature can include a spectral peak. The spectral signature can be identified when the spectral peak is above certain threshold, which can be predetermined by analyzing the reference solutions containing the chemical as described above. For example, a signal-to-noise ratio of the spectral peak relative to the noise background can be above 3 for the spectral signature to be positively identified.

It should be noted that the steps illustrated in FIG. 29 is compatible with and can incorporate one or more steps shown in FIG. 8, which involves using a sample solution containing nano particles.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention. For example, nano surface structures applicable to the disclosed systems and methods are not limited to the examples described. The nano surface structures can include nano rods (or columns), nano holes (or pores), and other nano surface textures, and a deposit of nano particles coated on a sensor surface.

The invention claimed is:

1. A method for detecting a chemical or biological substance, comprising:
   introducing a sample material into a sample solution containing nano particles and comprising multi-valence ions;
   illuminating the sample solution containing the sample material and the nano particles by a laser beam;
   collecting light scattered by the sample material and the nano particles in the sample solution;
   obtaining a Raman spectrum from the light scattered by the sample material and the nano particles in the sample solution;
   determining the existence of a spectral signature associated with a chemical or biological substance around a predetermined wavelength in the Raman spectrum; and
   identifying the chemical or biological substance in the sample material based on the spectral signature in the Raman spectrum.

2. The method of claim 1, further comprising: after the step of introducing, allowing molecules of the sample material to adsorb to the nano particles.

3. The method of claim 1, wherein the nano particles comprise a magnetic or ferromagnetic material.

4. The method of claim 3, wherein the nano particles comprise a material selected from a group consisting of iron, cobalt, and nickel.

5. The method of claim 1, further comprising applying an electrical field, a magnetic field, or an electro-magnetic field to the sample solution during at least a portion of the step of collecting.

6. The method of claim 5, wherein the electrical field, the magnetic field, or the electro-magnetic field is static or alternating.

7. The method of claim 1, wherein the nano particles comprise a material selected from a group consisting of a metal, a metal alloy, an oxide material, silicon, a polymeric material, and a combination thereof.

8. The method of claim 7, wherein the nano particles comprise a material selected from a group consisting of titanium oxide, silicon oxide, and zinc oxide.

9. The method of claim 7, wherein the nano particles comprise a material selected from a group consisting of Al, Ag, Au, Cu, Fe, Co, Ni, Cr, Zn, Sn, Pd, Pt, and a combination thereof.

10. The method of claim 1, wherein the nano particles have an average dimension in a range from about 1 nm to about 100 µm.

11. The method of claim 10, wherein the nano particles have an average dimension in a range from about 5 nm to about 500 nm.

12. The method of claim 1, wherein the nano particles have a size distribution characterized by an average dimension and a width, wherein the ratio of the width to the average dimension is in a range from about 0.01 to about 3.

13. The method of claim 1, further comprising introducing an ionic material into the sample solution, wherein the ionic material comprises an ion selected from a group consisting of $Ca^{++}$, $Ba^{++}$, $Sr^{++}$, $Mg^{++}$, $Mn^{++}$, $Al^{+++}$, $Zn^{++}$, $Sn^{++}$, and $Sn^{++++}$.

14. The method of claim 1, wherein the sample solution has an ionic concentration in a range from about 10 µM to a saturation level.

15. The method of claim 1, wherein the spectral signature includes at least one spectral peak around the predetermined wavelength in the Raman spectrum, the method further comprising determining a concentration of the chemical or biological substance using the spectral signature if the chemical or biological substance is determined to exist in the sample material.

16. The method of claim 1, wherein the sample material is extracted from a food product.

17. The method of claim 16, wherein the food product includes dairy products, candies, cookies, drinks, alcohol, meat, seafood, tea, fresh or canned vegetables, fruits, grain products, cereals, corn chips, potato chips, or protein containing food.

18. The method of claim 17, wherein the dairy products comprise milk, milk powders, cheese, cheese-containing cakes, yogurts, ice creams, milk containing candies, or cookies.

19. The method of claim 17, wherein the product comprises a dairy product, wherein the chemical or biological substance includes melamine or melamine cyanurate, wherein the spectral signature comprises one or more of spectral peaks around 678 $cm^{-1}$, 698 $cm^{-1}$, or 712 $cm^{-1}$, or around 1648 $cm^{-1}$.

20. The method of claim 16, wherein the chemical or biological substance comprises melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, or enorfloxacin.

21. The method of claim 1, wherein the sample material comprises a body fluid obtained from a person, the method further comprising: diagnosing a disease in the person based on the spectral signature determined in the Raman spectrum.

22. The method of claim 21, wherein the body fluid includes blood, saliva, urine, serum, tear, sweat, stomach fluid, sperm, or a secrete body fluid.

23. The method of claim 21, wherein the disease is selected from the group consisting of lung cancer, breast cancer, stomach cancer, liver cirrhosis, a failing kidney, ulcer cancer, ovarian cancer, uterus cancer, cervix cancer, oral cancer, esophageal cancer, thyroid cancer, larynx cancer, leukemia, colon cancer, bladder cancer, prostate cancer, bronchus cancer, pancreas cancer, head cancer, neck cancer, skin cancer, HIV(virus), diabetes, smoking status, and drug addiction.

24. The method of claim 21, wherein the disease includes an illicit use of a drug selected from a group consisting of heroin, methamphetamine, cocaine, caffeine, morphine, codeine, amphetamine, ephedrine, papaverine, narcotine, and MDMA.

25. The method of claim 1, wherein the nano particles comprise carbon nano tubes.

26. The method of claim 25, wherein the carbon nano tubes comprise single-walled or multiple walled carbon nano tubes, Fullerite, a torus, nanobuds, or nanoflowers.

27. A method for detecting a chemical or biological substance, comprising:
  introducing a sample material into a sample solution containing nano particles having an average dimension in a range from about 5 nm to about 500 nm, wherein the nano particles have a size distribution characterized by an average dimension and a width, wherein the ratio of the width to the average dimension is in a range from about 0.01 to about 3, wherein the nano particles comprise a magnetic or ferromagnetic material;
  introducing an ionic material comprising multi-valence ions into the sample solution;
  illuminating the sample solution containing the sample material and the nano particles by a laser beam;
  collecting light scattered by the sample material and the nano particles in the sample solution;
  obtaining a Raman spectrum from the light scattered by the sample material and the nano particles in the sample solution;
  determining the existence of a spectral signature associated with a chemical or biological substance around a predetermined wavelength in the Raman spectrum; and
  identifying the chemical or biological substance in the sample material based on the spectral signature in the Raman spectrum.

28. A method for detecting a chemical or biological substance, comprising:
  introducing a sample material into a sample solution, wherein the sample solution comprises nano particles having an average dimension in a range from about 5 nm to about 500 nm, wherein the nano particles have a size distribution characterized by an average dimension and a width, wherein the ratio of the width to the average dimension is in a range from about 0.01 to about 3;
  introducing an ionic material comprising multi-valence ions into the sample solution;
  illuminating the sample solution containing the sample material and the nano particles by a laser beam;
  collecting light scattered by the sample material and the nano particles in the sample solution;
  obtaining a Raman spectrum from the light scattered by the sample material and the nano particles in the sample solution;
  determining the existence of a spectral signature associated with a chemical or biological substance around a predetermined wavelength in the Raman spectrum; and
  identifying the chemical or biological substance in the sample material based on the spectral signature in the Raman spectrum.

* * * * *